US005278141A

United States Patent [19]

Berliner

[11] Patent Number: 5,278,141

[45] Date of Patent: * Jan. 11, 1994

[54] FRAGRANCE COMPOSITIONS CONTAINING HUMAN PHEROMONES

[75] Inventor: David L. Berliner, Atherton, Calif.

[73] Assignee: Erox Corporation, Menlo Park, Calif.

[ * ] Notice: The portion of the term of this patent subsequent to Dec. 21, 2010 has been disclaimed.

[21] Appl. No.: 28,727

[22] Filed: Mar. 8, 1993

Related U.S. Application Data

[63] Continuation of Ser. No. 856,435, Mar. 24, 1992, abandoned.

[51] Int. Cl.$^5$ .............................................. A61K 7/46

[52] U.S. Cl. ......................................... 512/3; 512/15; 512/19

[58] Field of Search ............................... 512/3, 15, 19

[56] References Cited

PUBLICATIONS

Berliner et al, J. Steroid Biochem. Molec. Biol., vol. 39, pp. 671-679 (1991).

Stensaas et al, J. Steroid Biochem. Molec. Biol., vol. 39, pp. 553-560 (1991).

Benjamin, Chem. Abst., vol. 96, #101,390q (1982).

Kirk-Smith et al, Chem. Abst., vol. 94, #115,047d (1981).

*Primary Examiner*—James H. Reamer

*Attorney, Agent, or Firm*—Morrison & Foerster

[57] ABSTRACT

The invention concerns novel, non-therapeutic fragrance compositions containing an odorant and a naturally occurring human pheromone. The invention also concerns fragrance compositions containing mixtures of naturally occurring human pheromones. The human pheromones disclosed are steroids which belong to two distinct chemical classes: 16-Androstenes and Estrenes.

23 Claims, 16 Drawing Sheets

III R = H

IV $R = COOCH_3$

4

5 $R^1 = OH$; $R^2 = H$ (48%)

6 $R^1 = H$; $R^2 = OH$ (48%)

9a

XIX

9

XX

10

11 $R^1$ = OH; $R^2$ = H (87%)

12 $R^1$ = H; $R^2$ = OH (87%)

VII

8

7

11 14 12 15 13 16 17

18

19 20 21 22

26

27

28

VII

23

24

25

FRAGRANCE COMPOSITIONS CONTAINING HUMAN PHEROMONES

This application is a continuation of application Ser. No. 07/856,435, filed Mar. 24, 1992, now abandoned.

FIELD OF THE INVENTION

This invention is generally related to the fields of personal care products, cosmetics and fragrances. More specifically, the invention concerns novel fragrance compositions and personal care products containing such fragrance compositions. This invention also pertains to the class of pheromones which are active in humans, and to the incorporation of pheromones into fragrance compositions.

BACKGROUND ART

The present invention relates to cosmetics, particularly fragrances, which contain human pheromones. Pheromones are biochemicals produced by an animal or individual which elicits a specific physiological or behavioral response in another member of the same species. Different pheromones are produced by the members of each sex and received by specialized receptors in the nasal passage of members of the opposite sex. The human pheromones referred to in this invention are certain 16-Androstene and/or Estrene steroids, some of which occur naturally in humans.

16-Androstene steroids are structurally related to testosterone, and are characterized by the elimination of the 17-hydroxyl of testosterone to a 16-ene moiety. Some members of this group have been reported to act as pheromones in some mammalian species—for instance, 5α-Androst-16-en-3α-ol and 5α-Androst-16-en-3-one in pigs (Melrose, D. R., et al., *Br. vet. J.* (1971) 127:497-502). These 16-Androstenes produced by the boar induce mating behavior in estrus sows (Claus, et al., *Experimentia* (1979) 35:1674-1675).

Some studies have noted that, in some species, various characteristics of certain 16-Androstenes (including 5α-Androst-16-en-3α-ol and 5α-Androst-16-en-3-one), such as blood concentration, metabolism, and localization, are sexually dimorphic (Brooksbank, et al., *J. Endocr.* (1972) 52: 239-251; Claus, et al., *J. Endocr.* (1976) 68:483-484; Kwan, et al., *Med. Sci. Res.* (1987) 15:1443-1444). For instance, 5α-Androst-16-en-3α-ol and 5α-Androst-16-en-3-one, as well as 4,16-Androstadien-3-one, have been found at different concentrations in the peripheral blood, saliva and axillary secretions of men and of women (Kwan, T. K., et al., *Med. Sci. Res.* (1987) 15:1443-1444).

The possible function of some 16-Androstenes as human pheromones, to the extent of effecting choice and judgment, has been suggested (Id.; see also Gower, et al., "The Significance of Odorous Steroids in Axillary Odour", in, *Perfumery,* pgs 68-72, Van Tolier and Dodd, Eds., Chapman and Hall, 1988); Kirk-Smith, D. A., et al., *Res. Comm. Psychol. Psychiat. Behav.* (1978) 3:379). Androstenol (5α-Androst-16-en-3α-ol) has been claimed to exhibit a pheromone-like activity in a commercial men's cologne and women's perfume (Andron TM for Men and Andron TM for Women by Jövan). Japanese Kokai patent, application No. 2295916, refers to perfume compositions containing androstenol and/or its analogue. 5,16-Androstadien-3β-ol (and perhaps the 3α-ol) has also been identified in human axillary secretion (Gower, et al., Supra at 57-60.

Estrene steroids are typified by 17β-Estradiol (1,3,5(10)-Estratrien-3,17β-diol), and are characterized by a phenolic 1,3,5(10) A-ring and a hydroxy or hydroxy derivative, such as an ether or ester, at the 3-position. The pheromone properties of some estrene steroids for some mammalian species has been described. Michael, R. P. et al., *Nature* (1968) 218:746 refers to estrogens (particularly estradiol) as a pheromonal attractant of male rhesus monkeys. Parrot, R. F., *Hormones and Behavior* (1976) 7:207-215, reports estradiol benzoate injection induces mating behavior in ovariectomized rats; and the role of the blood level of estradiol in male sexual response (Phoenix, C. H., *Physiol. and Behavior* (1976) 16:305-310) and female sexual response (phoenix, C. H., *Hormones and Behavior* (1977) 8:356-362) in Rhesus monkeys has been described.

The human pheromones described in this application have been referred to previously in applicant's U.S. Ser. No. 07/707,862, filed May 5, 1991, U.S. Ser. No. 07/708,936, filed May 31, 1991, P.C.T. application No. PCT/US92/00219, filed Jan. 7, 1991, and P.C.T. application No. PCT/US92/00220 , filed Jan. 7, 1991, all of which are pending and are incorporated by reference.

The most likely means of communication of a putative human pheromone is the inhalation of a naturally occurring pheromone present on the skin of another. Several 16-Androstene steroids, including 5α-Androst-16-en-3α-ol and, 5α-Androst-16-en-3-one, 4,16-Androstadien-3-one, 5,16-Androstadien-3α-ol, and perhaps 5α-Androstadien-3α-ol, are naturally occurring in humans and may be present on the skin. It is estimated that the naturally occurring maximum concentration of all 16-Androstene steroids on human skin is from 2 to 7 ng/cm$^2$. During intimate contact it is estimated that a human would be exposed to no more than 700 ng of a naturally occurring steroid. Since these compounds are relatively non-volatile, it is estimated that, even during intimate contact, a human subject would inhale no more than 0.7 pg of a naturally occurring steroid from the skin of another. The subject invention is effective because it delivers a much larger amount of the active pheromone steroids than does normal intimate contact between individuals.

There is however, little agreement in the literature as to whether or not any putative pheromone actually plays a role in the sexual or reproductive behavior of mammals, particularly of humans. See: Beauchamp, G. K., et al., "The Pheromone Concept in Mammalian Chemical Communication: A Critique", in: *Mammalian Olfaction, Reproductive Processes, and Behavior,* Doty, R. L., Ed., Academic Press, 1976. See also, Gower, et al., supra at 68-73.

Receptors for pheromones are found in the vomeronasal organ (VNO), a small structure which opens to the nasal passage in normal individuals (Moran, D. T., et al., *J. Steroid Biochem. and Molec. Biol.* (1991) 39:545; Stensaas, L. J., et al., *J. Steroid Biochem. and Molec. Biol.* (1991) 39:553; Garcia-Velasco, et al., *J. Steroid Biochem. and Molec. Biol.* (1991) 39:561). An odor does not bind to a VNO receptor—only a pheromone. A pheromone-specific change in the electrical potential of VNO receptor epithelium can be measured as described by Monti-Bloch, L., et al. (*J. Steroid Biochem. and Molec. Biol.* (1991) 39:573). This receptor binding activity is an essential characteristic of an active pheromone.

The compositions of many commercial perfumes and fragrances contain mammalian pheromones. Since pheromones are generally species specific, the mammalian pheromones found in commercial perfumes do not function as a pheromone, but instead provide a fixative note in the overall composition of the fragrance. Thus the perfumes, personal care products and cosmetics now available do not bind to pheromone receptors in the VNO and do not stimulate the vomeronasal nerve which communicates with the hypothalamus of the brain. Furthermore, in some cases the use of animal pheromones, or synthetics related to animal pheromones, may cause skin irritations or allergic responses in some individuals. Still further, since the source of animal pheromones used in fragrances are the anal glands of the contributing animal some individuals find it objectionable to use these substances. Finally, since none of the major ingredients found in commercial fragrances occur naturally on the human skin, the resulting scents are not natural human scents.

It would be preferable for a fragrance to contain naturally occurring human pheromones since this would result in stimulation of both olfactory (scent) receptors and pheromone receptors, would reduce the likelihood of irritation or an allergic response, would provide a more attractive composition for personal application, and would have a more natural human scent.

SUMMARY OF THE INVENTION

Accordingly, it is a primary object of the invention to address the above-mentioned needs in the art by providing a fragrance composition containing a naturally occurring human pheromone.

It is also an object of this invention to provide fragrance compositions which stimulate both olfactory receptors and pheromone receptors in the VNO.

It is another object of this invention to provide fragrance compositions which are unlikely to be irritating to the skin of individuals and are likely to be hypoallergenic.

It is another object of this invention to provide a fragrance composition with the consumer appeal of a naturally occurring human pheromone.

It is another object of this invention to provide a fragrance composition with a natural human scent.

Additional objects, advantages and novel features of the invention will be set forth in part in the description which follows, and in part will become apparent to those skilled in the art upon examination of the following, or may be learned by practice of the invention.

The objects of this invention are achieved by providing a non-therapeutic, fragrance composition containing a perfumery odorant and a human pheromone. The pheromone generates an in vivo vomeronasal organ receptor binding potential in a human subject.

The objects of this invention are also achieved by providing a non-therapeutic fragrance composition containing a perfumery odorant and a steroidal compound selected from the group consisting of Androsta-4,16-dien-3-one, Androsta-4,16-dien-3α-ol, Androsta-4,16-dien-3β-ol, 19-nor-4,16-Androstadien-3-one, 19-nor-10-OH-4,16-Androstadien-3-one, 19-OH-4,16-Androstadien-3-one, 5,16-Androstadien-3β-ol, 5α-5,16-Androstadien-3α-ol, 19-nor-16-Androsten-3-one, 19-nor-16Androsten-3α-ol, 19-nor-16-Androsten-3β-ol, 1,3,5(10)-Estratrien-3,17β-diol, 1,3,5(10)-Estratrien-3,16α,17β-triol, 1,3,5(10)-Estratriene-3-ol-17-one, or 1,3,5(10),16-Estratetraen-3-ol, and any combinations thereof.

DETAILED DESCRIPTION

Figure 1:
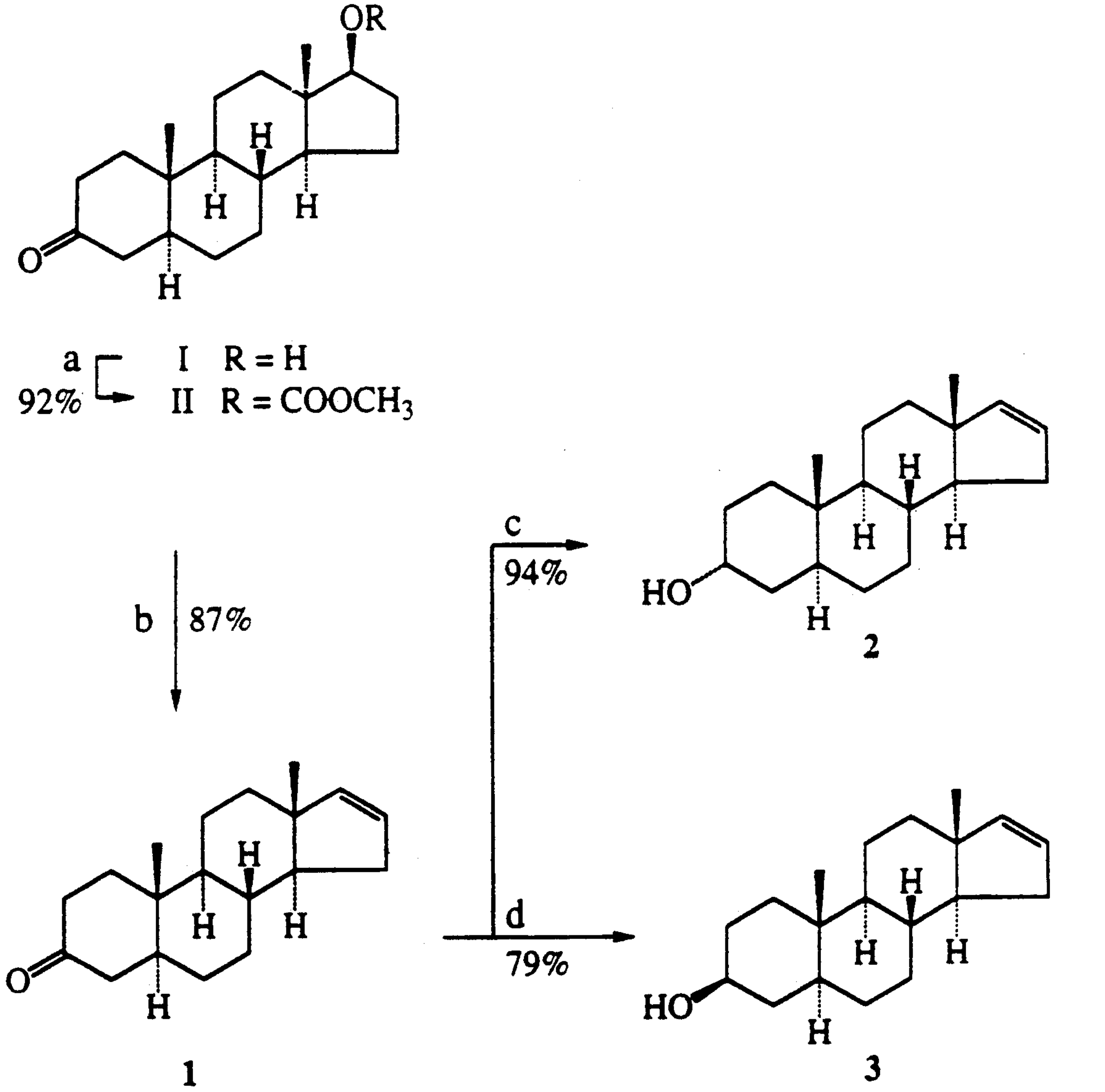
FIG. 1 schematically illustrates the synthesis of 5α-Androst-16-en-3-one, 5α-Androst-16-en-3α-ol and 5α-Androst-16-en-3β-ol.

Before the present compositions are disclosed and described, it is to be understood that this invention is not limited to specific fragrances, specific steroidal compounds, or the like, as such components may, of course, vary. It is also to be understood that the terminology used herein is for the purpose of describing particular embodiments only and is not intended as limiting.

It must be noted that, as used in the specification and the appended claims, the singular form "a", "an" and "the" include plural referents unless the context clearly dictates otherwise. Thus, for example, reference to "a perfumery odorant" includes mixtures of perfumery odorants, reference to "a human pheromone" includes mixtures of human pheromones, and the like.

A. Definitions

An "odour" is any scent or smell, whether pleasant or offensive. An odour is consciously perceived by an individual when odorant molecules bind to the olfactory epithelium of the nasal passage. An "odorant" is an odorous substance. Perfumery materials, whether natural or synthetic, are described as odorants. A "perfumery odorant" is an odorant used for the principal purpose of providing a odor. A "scent" is the odour left behind by an animal or individual. People use perfumes to augment their natural scent.

A "perfume" or a "fragrance composition" is a specific pleasantly odorous cosmetic composition for topical application to an individual. Technically, perfumes are mixtures of a variety of substances, and may include natural materials of vegetable or animal origin, wholly or partly artificial compounds, or mixtures thereof. Dissolved in alcohol, these mixtures of various volatile fragrant substances release their scents into the air at normal temperatures. To a perfumer, only the extrait—the mixture which contains the highest proportion of fragrance concentrate and the least possible alcohol—is called perfume. Mixtures of lower concentration include eau de parfum, after shave, eau de toilette, eau de sport, splash cologne, eau de cologne, cologne, eau fraiche, and the like. In addition to the fragrance solutions which are diluted with alcohol, there are also those which are diluted with oil. Furthermore, compact and cream perfumes are produced by mixing up to 25% fragrance oil with solids such as paraffin or other waxes. Generally all the fragrance compositions described above are referred to as perfumes, and that is how the term is used herein.

A "pheromone" is a biochemical produced by an animal or individual which elicits a specific physiological or behavioral response in another member of the same species. In addition to physiological responses, pheromones can be identified by their species specific binding to receptors in the vomeronasal organ (VNO). The binding of pheromones is generally sexually dimorphic. Naturally occurring human pheromones induce sexually dimorphic changes in receptor binding potential in vivo in the human VNO.

"Sexually dimorphic" refers to a difference in the effect of, or response to, a compound or composition between males and females of the same species.

The "vomeronasal organ" is a cul-de-sac which opens to the nasal passage and contains specialized receptor cells for pheromones.

B. Perfumes

The art and science of perfumery has been developed over several hundred years and is now well established. A brief summary of perfumery is provided herein. This subject is treated more fully in many publications including Wells, F. V. and M. Billot, *Perfumery Technology,* Ellis Horwood, Ltd., publisher, 2nd Ed. 1981.

1. Types of ingredients

The diversity of the non-animal, natural products used in perfumery is considerable. In addition, advances in organic chemistry in the later nineteenth and the twentieth centuries have provided an equally broad diversity of artificial odorants as well as the ability to synthesize some of the naturally occurring components of natural odorants. Most perfumes combine preparations of naturally occurring materials with synthetic odorants.

The natural odorants that are generally employed in perfumery come from both animal and vegetable materials and can be assigned to the following six categories based on how they are treated:

1) Concrete oils—extracted with hydrocarbon solvents, without heat;
2) Absolute oils—alcohol extracted from concrete oils, without heat;
3) Essential oils—distilled from naturally occurring materials;
4) Expressed oils—physically removed directly from the natural material;
5) Islates—fractionally distilled from essential oils;
6) Tinctures—obtained by prolonged alcohol extraction of naturally occurring materials.

A perfumer will typically have numerous oils, isolates, and tinctures from a variety of natural sources within each category. The perfumer will also have a vast array of artificial odorants and synthetics of naturally occurring compounds. Each of these materials is referred to as a "note". The art of perfumery involves the mixing of these various notes to produce a finished fragrance.

While there are many subjective approaches to the formulation of a perfume, most seem to incorporate the notion of top notes, middle notes and bass notes. Top notes are very volatile and lack tenacity, or staying power. Middle notes are somewhat lower in volatility and are used as modifiers of the top notes. Bass notes are still lower in volatility and are long-lasting in odorous effect. Bass notes are also referred to as fixatives of the fragrance. Notes of animal origin, or artificials which mimic animal notes, are usually bass notes.

2. Animal notes

Many commercial perfumes contain notes from animal sources, usually pheromones of the species from which the material is obtained, or synthetics and artificial notes which mimic the characteristics of animal notes. The principal animal-derived notes are the following:

1) musk—derived from the scent gland of the musk deer;
2) civet—obtained as a glandular secretion of the civet cat;
3) castoreum—obtained from the preputial follicle of the beaver; and
4) ambergris—a regurgitated or excreted material obtained from sperm whales.

The first three are pheromones for the species of origin, but since pheromones are species specific, they do not induce any pheromone-related behavior in humans. Animal notes are used as a fixative for the perfume fragrance. As a concentrate the odor of animal notes may not be pleasing, but when diluted, they contribute to the fragrance of the final product.

3. Human Pheromones

In the subject invention, naturally occurring human pheromones are used instead of, or in addition to animal pheromones, or their derivatives or homologues. Naturally occurring human pheromones have several advantages.

The perfumed products now available do not stimulate VNO receptors since an odorant which is not a pheromone for humans stimulates only the olfactory receptors of the nose. Fragrance compositions which are both pleasant smelling and also contain human pheromones will stimulate both olfactory receptors, and pheromone receptors in the VNO of individuals. Such a fragrance composition provides a broader olfactory stimulation than previously possible.

Perfumes are applied to the skin; however, the living skin, with its excretory and respiratory mechanisms, its secretions and variable temperature, is too changeable a medium to act as a good carrier of perfumes and frequently distorts the odour of the perfume in contact with it. Since human pheromones are normally present on human skin, a fragrance composition containing human pheromones would provide a more stable scent on the skin. Furthermore, the resulting scent would smell more naturally human.

Some ingredients associated with commonly used animal notes (e.g. benzyl benzoate, paracresol, nitromusks) have been found to cause skin irritation in some individuals. Furthermore, some individuals report an allergic response to some perfumes. Fragrance compositions containing naturally occurring human pheromones would be less likely than commonly used animal-related components to cause irritation or allergic response.

Finally, a perfume which uses naturally occurring human pheromones rather than material derived from the anal or preputial glands of animals would be inherently more appealing to many consumers.

As a concentrate, pheromones may or may not have a detectable odor. Since they bind to receptors which are physically and functionally distinct from olfactory receptors, they may or may not carry their own smell. However, some of the pheromones described herein do in fact have an odor. As a concentrate, the odor of these pheromones may not necessarily be pleasant. Thus, when diluted in a perfume the practical upper concentration limit is determined by the pleasantness of the resulting fragrance. Generally, human pheromones are present in the fragrance composition of the subject invention at a concentration of no more than about 200 μg/ml, more commonly no more than about 100 μg/ml, preferably no more than about 50 μg/ml, and more preferably no more than about 25 μg/ml.

Pheromones have a very low threshold of detectable receptor binding and they are effective at low concentrations. Generally, human pheromones are present in the fragrance composition of the subject invention at a concentration of at least about 50 ng/ml, more commonly at least about 100 ng/ml, preferably at least about 500 ng/ml, more preferably at least about 1 μg/ml.

C. Perfuming Other Products

Perfumes are commonly used per se as a personal care product. However, perfumes can be used in a variety of personal care products, household products and industrial products. The use of perfumes containing naturally occurring human pheromones in these other products falls within the scope of the subject application.

More particularly, fragrances containing human pheromones can be used in the preparation of cosmetics, make-up preparations, toilet and beauty preparations, bath and beauty soaps, bath oils, face and body creams and oils, underarm deodorants and the like. Fragrances containing human pheromones may also be used as environmental odorants as in air fresheners and deodorants, as a marketing promotion for merchandise (e.g. new cars, market displays, etc.), and the like.

The uses of fragrance compositions containing human pheromones, as provided herein, are examples of alternative uses which fall within the intended scope of the claims and do not limit the intended scope of use of this invention.

D. Human Pheromones

As described herein human pheromones generate a change in receptor potential in the VNO of human subjects. The naturally occurring human pheromones identified to date are steroids which fall into two classes—16-androstenes and estrenes. The biological activity of human pheromones is sexually dimorphic. 16-androstene pheromones generate a greater change in receptor potential of women than of men. Conversely, estrene pheromones generate a greater change in the receptor potential of men than of women.

16-Androstene steroids are aliphatic polycyclic hydrocarbons characterized by a four-ring steroidal structure with a methylation at the 13- position, and a double bond between the 16- and 17- positions. An androstene steroid is commonly understood to mean that the compound has at least two methylations, at the 13-position and the 10-position, thereby creating 18-position and 19-position carbons respectively. Unless a compound is explicitly described as "19-nor" it is understood that the compound does have a 19- carbon group. However, it is intended that 19-nor-16-Androstenes are generally regarded as 16-Androstene steroids for the purpose of the present invention.

Estrene steroids are aliphatic polycyclic hydrocarbons with a four-ring steroidal structure, a aromatic 1,3,5(10) A-ring, a methylation at the 13-position and a hydroxyl at the 3-position.

In describing the location of groups and substituents of 16-Androstene and Estrene steroids, the following numbering system will be employed.

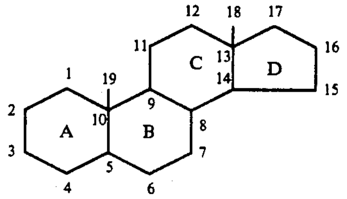

1. 16-Androstenes Useful in Conjunction With the Invention

The invention is directed to fragrance compositions containing a human pheromone which may be included in a group of Androstene steroids structurally related to testosterone (17-hydroxy-$\Delta^4$-androstene-3-one), and to combinations of Androstene and Estrene steroids. All Androstenes within the group can be distinguished from testosterone by elimination of 17-OH to 16-ene. The group is referred to herein as 16-Androstenes.

These 16-Androstenes have the formula:

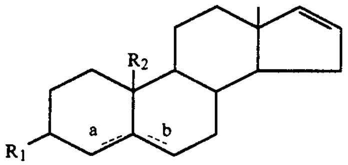

I wherein $R_1$ is selected from the group consisting of oxo, α-hydroxy, and β-hydroxy; $R_2$ is selected from the group consisting of hydrogen, hydroxy, acyl, acyloxy, alkoxy, lower alkyl, methyl, hydroxyalkyl, hydroxymethyl, acyloxyalkyl, acyloxymethyl, alkoxyalkyl, and alkoxymethyl; and "a" and "b" are alternative sites for an optional double bond.

These 16-Androstenes may be distinguished from each other by variations at the 3-position ($R_1$ of formula I), 5-position (determinative of "a" or "b" the two optional, alternative double bonds (Δ4 and Δ5/6) of formula I), and the 10-position ($R_2$ of formula I). Preferred embodiments include $^{4,16}$Androstadien-3-one ($R_1$=oxo, a=double bond, $R_2$=methyl, commercially available from Steraloids, Inc., also referred to as Androstadienone), and 19-hydroxy-$^{4,16}$androstadien-3-one ($R_1$=oxo, a=double bond, $R_2$=hydroxymethyl), $^{4,16}$Androstadien-3α(β)-ol ($R_1$=hydroxy, a=double bond, $R_2$=methyl), 19-nor-$^{4,16}$Androstadien-3-one ($R_1$=oxo, a=double bond, $R_2$=hydrogen), and 19-nor-10-OH-$^{4,16}$Androstadien-3-one ($R_1$=oxo, a=double bond, $R_2$=hydroxy), syntheses of which are described herein).

2. Estrenes Useful in Conjunction With the Invention

The invention is additionally directed to fragrance compositions containing a human pheromone which may be included in a group of Estrene steroids, or to combinations of Estrene and 16-Androstene steroids. These Estrenes are structurally related to estradiol (also referred to as 1,3,5(10)-Estratriene-3,17β-diol). These Estrenes are distinguished from estradiol by elimination of 17-OH to 16-ene.

These Estrenes have the formula:

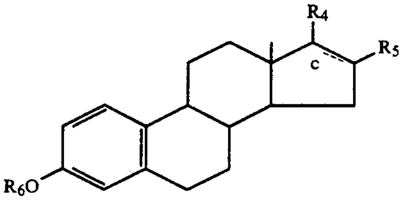

II wherein $R_4$ is selected from the group consisting of hydrogen, alkyl, oxo, α-hydroxy, β-hydroxy, cypionate, acetate, sulfate and glucuronide; $R_5$ is selected from the group consisting of hydrogen, α-hydroxy, and β-hydroxy; $R_6$ is selected from the group consisting of hydrogen, lower alkyl, benzoyl, cypionyl, acetyl, glucuronide, lower acyl and sulfate; and "a" is an optional double bond.

These Estrenes can be distinguished from each other by variations at the 3-position, variations at the 17-position and variations at the 16-position, with an optional double bond at the 16-position. Preferred embodiments include 1,3,5(10)-Estratriene-3,17β-diol; 1,3,5(10)-Estratriene-3,16α,17β-triol; 1,3,5(10)-Estratrien-3-ol-17-one; and 1,3,5(10),16-Estratetraen-3-ol. These steroids are compounds known in the art and are commercially available e.g. from Sigma Chemical Co., Aldrich Chemical Co., etc. 1,3,5(10),16-Estratetraen-3-ol is available from Research Plus, Inc. and from Steraloids, Inc.

E. Synthesizing Human Pheromones

As indicated in Section D1, above, some of the preferred 16-Androstene pheromones are not commercially available. Their syntheses are provided herein.

1. Synthetic Methods a. Preparation of 3-position, 5-position, and 19-nor derivatives As shown in formula I, above, the compounds used in the methods of the present invention are 16-Androstene steroids substituted at the 3-, 5-, and 19-positions. Many of the 3- and 5- substituted steroids are known compounds which may be derived from 17-hydroxy- and 17-oxo-steroids (commercially available e.g. from Aldrich Chemical Co) by elimination or reduction to the Δ16compound. The syntheses of most of these compounds are described by Ohloff (supra). As shown in FIG. 1, 17β-hydroxy-5α-androstan-3-one (I) and methyl chloroformate (a) in pyridine gives the methyl carbonate, 17β-methoxycarbonyloxy-5α-androstan-3-one (II) which provides a starting material for the 5α-androst-16-en-(3-one (1) and 3-ols (2,3)) (Ohloff, supra at pg 200).

Alkoxy derivatives are prepared from their corresponding hydroxy steroids by reaction with an alkylating agent such as trimethyloxonium fluoroborate, triethyloxonium fluoroborate or methylfluorosulfonate in an inert chlorocarbon solvent such as methylene chloride. Alternatively, alkylating agents such as alkyl halides, alkyl tosylates, alkyl mesylates and dialkylsulfate may be used with a base such as silver oxide or barium oxide in polar, aprotic solvents as for example, DMF, DMSO and hexamethylphosphoramide.

General procedures for synthetic reactions of steroids are known to those skilled in art (See for example, Fieser, L. F. and M. Fieser, *Steroids*, Reinhold, N.Y. 1959). Where time and temperature of reactions must be determined, these can be determined by a routine methodology. After addition of the required reagents, the mixture is stirred under an inert atmosphere and aliquots are removed at hourly intervals. The aliquots are analyzed by means of thin-layer chromatography to check for the disappearance of starting material, at which point the work-up procedure is initiated. If the starting material is not consumed within twenty-four hours, the mixture is heated to reflux and hourly aliquots are analyzed, as before, until no starting material remains. In this case the mixture is allowed to cool before the work-up procedure is initiated.

Purification of the products is accomplished by means of chromatography and/or crystallization, as known to those skilled in the art.

1. Synthesis of 10-Hydroxy-$\Delta^{4,16}$-Androstadien-3-one

Figure 3:
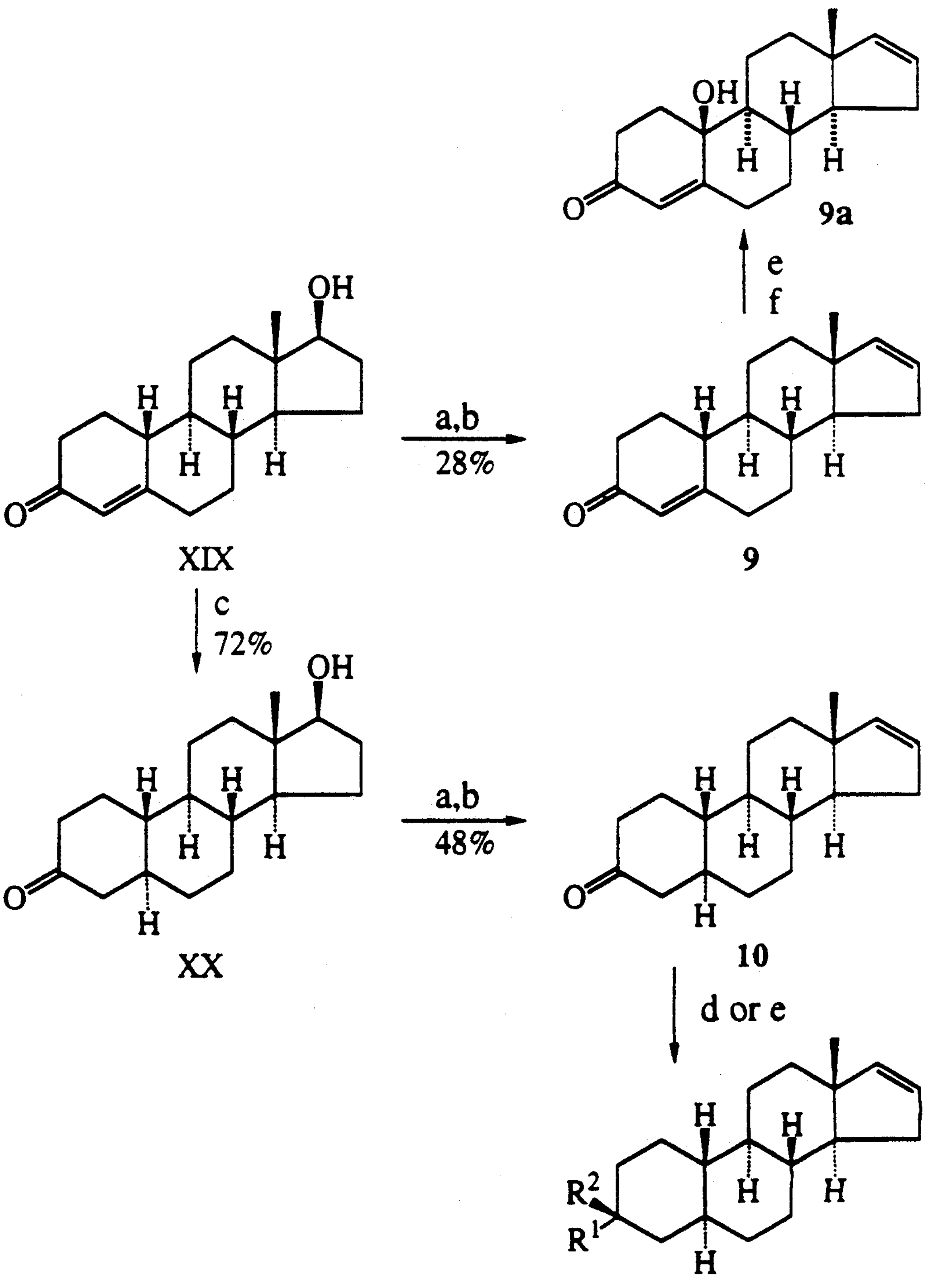
FIG. 3 schematically illustrates the synthesis of 19-nor-$\Delta^{4,16}$-Androstadien-3-one, 19-nor-$\Delta^{16}$-Androsten-3-one, 19-nor-Δ16-Androsten-3α-ol, 19-nor-Δ16-Androsten-3β-ol, and 19-nor-10-OH-$\Delta^{4,16}$-Androstadien-3-one.

As depicted in FIG. 3, 19-nor-$\Delta^{4,16}$-androstadien-3-one (9) in tetrahydrofuran is treated with one equivalent of lithium isopropylcyclohexylamide (LICA) (e), followed by molybdenum pentoxide in hexamethylphosphoramide/pyridine (MOOPH) (f). Aqueous work-up is followed by extraction and purification to yield 10-Hydroxy-$\Delta^{4,16}$-androstadien-3-one (9A). The procedure follows that of Vedejs, *J. Org. Chem.* (1978) 43:188.

b. Preparation of 19-OH Derivatives

1. Synthesis of 19-OH-$\Delta^{4,16}$-Androstadien-3-one

This compound has been disclosed as an intermediate in the synthesis of 19-oxo-3-aza-A-homo-5β-androstane (Habermehl, et al., *Z. Naturforsch.* (1970) 25b:191–195). A method of synthesizing this compound is provided. Additional methods of synthesis are provided in Examples 12 and 13.

EXAMPLES

The following examples are provided for illustrative purposes and should not be construed as limitations of the invention described in this application.

Abbreviations used in the examples are as follows: aq.=aqueous; RT.=room temperature; PE=petroleum ether (b.p. 50°-70°); DMF=N,N-dimethylformamide; DMSO=dimethyl sulfoxide; THF=tetrahydrofuran.

Example 1—5α-Androst-16-en-3-one (1)

This synthesis is depicted in FIG. 1. A solution of the methyl carbonate, 17β-methoxycarbonyloxy-5α-androstan-3-one (II) (9.6 g, 27.6 mmol) in toluene (200 ml) was pyrolyzed (b) in a Pyrex glass column (1=10 m, φ=9 mm) at 480° ($N_2$ stream ca. 11 ml/min) at a rate of ca. 1 g/h. The crude product (collected in two liquid $N_2$-cooled traps) was washed with sat. aq. $NaHCO_3$- and NaCl-solution, dried ($Na_2SO_4$) and evaporated. The residue (7.24 g, 97%) was recrystallized from PE at 0° to give 6.42 g (87%) of 1. An analytical sample was recrystallized from acetonitrile at RT. M.p. 142°-144°, $[a]_D=+35.6°$ (c=1.15) ([2]: m.p. 140°-141°, $[a]_D^{17}=+38°$ (c=2.08)). —IR. ($CDCl_3$): 1710s, 1595w. —$^1$H-NMR. (360 MHz): 0.79 (s, 3 H); 1.05 (s, 3 H); 5.70 (m, 1 H); 5.84 (m, 1 H).

Example 2—5α-Androst-16-en-3α-ol (2)

This synthesis is depicted in FIG. 1. To a 1M solution of lithium tris (1,2 dimethylpropyl) hydridoborate (c, commercially available from Aldrich, 2.5 ml, 2.5 mmol) at −55°, under $N_2$, was added a solution of ketone 1 (500 mg, 1.84 mmol) in THF (7ml) and the mixture was allowed to warm up to RT. After 3 h, the mixture was cooled to −55° and hydrolyzed by addition of water (1 ml), followed by EtOH (3 ml). The boranes were oxidized by adding to the mixture at −55° 10% aq. NaOH-solution (5 ml), followed by 30% aq. $H_2O_2$-solution (3 ml), and stirring for 3 h at RT. Cyclohexane (100 ml) was added and the organic phase washed successively with water, sat. aq. $NaHSO_3$-solution and sat. aq. NaCl-solution; after drying ($Na_2SO_4$) and evaporation of the solvent, the residue was chromatographed on silica gel (60 g) with toluene/ethyl acetate 2:1. The axial alcohol 2 was eluted first (443 mg, 89%) and the second fraction contained the equatorial alcohol 3 (24 mg, 4.8%). An analytical sample of z was recrystallized from PE at 0°. M.p. 142°-144°, $[a]_D=+15°$ (c=1.33) ([2]: m.p. 143.5°-144°, $[a]_D^{16}=+13.9°$ (c=0.94)). —IR. ($CDCl_3$): 3625m, 3450w, 1590w. —$^1$H-NMR. (360 MhZ): 0.77 (s, 3 H); 0.82 (s, 3H); 4.03 (m, $w_{½}\approx 8$, 1 H); 5.70 (m, 1 H); 5.83 (m, 1 H).

Example 3—5α-Androst-16-en-3β-ol (3)

This synthesis is depicted in FIG. 1. Ketone 1 (500 mg, 1.84 mmol) Was reduced with sodium borohydride (d, 75 mg, 2 mmol) in THF/MeOH 5:1 (18 ml) at RT (2 h). The crude product was chromatographed on silica gel (60 g) using toluene/ethyl acetate 2:1. After traces of the axial alcohol 2 (9 mg, 2%) were observed, the pure equatorial alcohol 3 (388 mg, 77%) was eluted. An analytical sample was recrystallized from MeOH/water. M.p. 124°-125°, $[a]_D=+14.2°$ (c=1.12) ([2]: m.p. 125°-127°, $[a]_D^{17}=+11.2°$ (c=0.76)). —IR. ($CDCl_3$): 3620m, 3430w, 1590w. —$^1$H-NMR. (360 Mhz): 0.77 (s, 3 H); 0.85 (s, 3 H); 3.60 t×t, J=11 and 5, 1 H); 5.70 (m, 1 H); 5.84 (m, 1 H).

Example 4—Androsta-4,16-dien-3-one (4)

Figure 2:
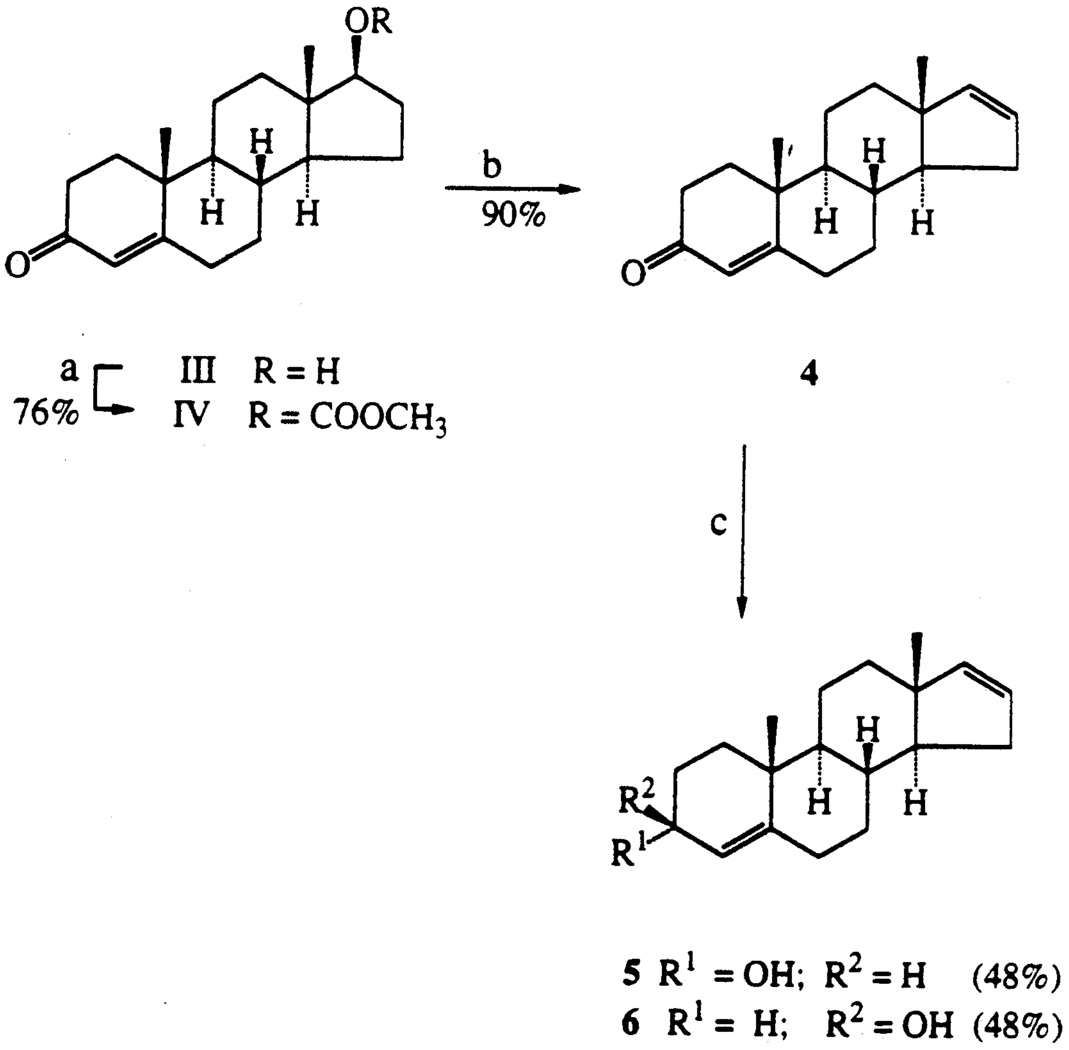
FIG. 2 schematically illustrates the synthesis of Androsta-$\Delta^{4,16}$-dien-3-one, Androsta-$\Delta^{4,16}$-dien-3α-ol, and Androsta-$\Delta^{4,16}$-dien-3β-ol.

This synthesis is depicted in FIG. 2. Several methods are known for the conversion of testosterone into Androsta-4,16-dien-3-one (Brooksbank et al., *Biochem. J.* (1950) 47:36). Alternatively, thermolysis (460°) of the methyl carbonate of testosterone gives Androsta-4,16-dien-3-one in 90% yield. 17β-Methoxycarbonloxy-androst-4-en-3-one (IV) was prepared from testosterone (III. Fluka) with methyl chloroformate/pyridine (a) in 76% yield (after recrystallization from MeOH). M.p. 140°-141°, $[a]_D=95.4°$ (c=1.10) —IR. ($CDCl_3$): 1740s, 1665s, 1450s, 1280s, —$^1$H-NMR. (360 Mhz): 0.87 (s, 3 H); 1.20 (s, 3 H); 3.77 (s, 3 H); 4.53 (br. t, J=8, 1H); 5.75 (s, 1 H). A solution of the methyl carbonate IV in toluene was pyrolyzed (b) as described for 1 Recrystallization of the crude product from acetone at RT. gave pure ketone 4 in 90% yield. M.p. 127°-129.5°, $[a]_D=+118.9°$ (c=1.32) ([3]: m.p. 131.5°-133.5° (hexane), $[a]_D^{16}=+123\pm3.5°$ (c=1.03)). —IR. ($CDCl_3$): 3050w, 1660s, 1615m. —$^1$H-NMR. (360 Mhz): 0.82 (s, 3 H); 1.22 (s, 3 H); 5.70 (m, 1 H); 5.73 (s, 1 H); 5.84 (m, 1 H).

Example 5—Androsta-4,16-dien-3α-ol (5) and -3β-ol (6)

These syntheses are depicted in FIG. 2. Androsta-4,16-dien-3-one (4) was reduced at −55° with lithium tris(1,2-dimethylpropyl)hydridoborate in THF (c) as described for the preparation of 2 (FIG. 1). Chromatography on silica gel with $CH_2Cl_2$/ethyl acetate 9:1 gave pure axial alcohol 5 (48% yield) and pure equatorial alcohol 6 (48% yield). Analytical samples were further purified by recrystallization (from PE at −30° for 5, from cyclohexane at RT. for 6).

Data of 5. M.p. 77°-79°, $[a]_D=+120.6°$ (c=1.26) —IR. ($CDCl_3$): 3620m, 3440m br., 1660m, 1595w. —$^1$H-NMR. (360 MHz): 0.79 (s, 3 H); 1.02 (s, 3 H); 4.07 (m, $w_{½}\approx 10$, 1 H); 5.48 (d×d, J=5 and 2, 1 H); 5.71 (m, 1 H); 5.85 (m, 1 H).

Data of 6. M.p. 116°-119°, $[a]_D=+53.9°$ (c=1.28) ([47]: m.p. 116°-118°, $[a]_D=+59.3°$ (c=0.4) —IR. ($CDCl_3$) 3610m, 3420m br., 3050m, 1660m, 1590w. —$^1$H-NMR. (360 Mhz): 0.78 (s, 3 H); 1.08 (s, 3 H); 4.15 (m, $w_{½}\approx 20$, 1 H); 5.30 (m, $w_{½}\approx 5$, 1 H); 5.71 (m, 1 H); 5.85 (m, 1 H).

Example 6—Androsta-$\Delta^{5,16}$-dien-3α-ol (7)

Figure 4:
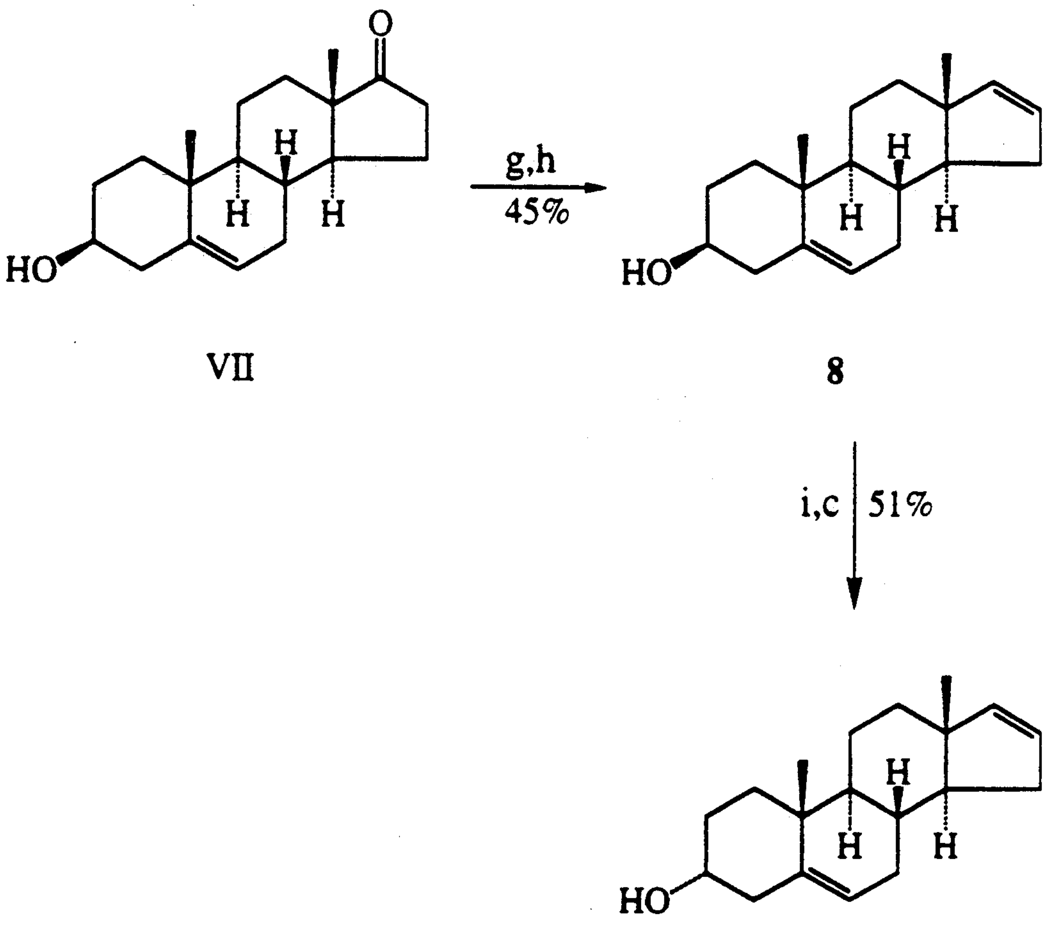
FIG. 4 schematically illustrates the synthesis of Androsta-$\Delta^{5,16}$-dien-3α-ol and Androsta-$\Delta^{5,16}$-dien-3β-ol.

This synthesis is depicted in FIG. 4. To a solution of alcohol 8 (545 mg, 2.0 mmol) in acetone (100 ml) at 0° under $N_2$ was added rapidly Jones reagent (i, 1.5 ml, ca. 4 mmol). After 5 min., the mixture was poured into a dilute phosphate buffer (Ph 7.2, 1200 ml) and extracted with ether. The extracts were washed with sat. aq. NaCl-solution, dried ($Na_2SO_4$) and evaporated to give mainly Androsta-5,16-dien-3-one as an oil (567 mg). The crude product was dissolved in THF (7 ml) and reduced with lithium tris (1,2-dimethylpropyl) hydridoborate (c) at −55° as described for the preparation of 2. The crude product (530 mg) was chromatographed on silica gel (100 g) with $CH_2Cl_2$/ethyl acetate 4:1 to give 280 mg (51%) of pure a-alcohol 7 (eluted first) and 13 mg of starting alcohol 8. A small sample of 7 was recrystallized from acetone/water at RT. M.p. 138°, $[a]_D=-77.5°$ (c=1.2). —IR. ($CDCl_3$): 3580m, 3430m, 1665W, 1590w, —$^1$H-NMR. (360 Mhz): 0.80 (s, 3 H); 1.06 (s, 3 H); 4.02 (m, $w_{½}\approx 8$, 1 H); 5.44 (m, 1 H); 5.72 (m, 1 H); 5.86 (m, 1 H).

Example 7—$\Delta^{5,16}$-Androstadien-3β-ol (8)

This synthesis is depicted in FIG. 4. This compound was prepared in 73% yield by a known procedure (Marx, A. F., et al., Ger. Offen. 2,631,915; Chem. Abst. 87:23614p (1977)) from commercial [Fluka) 3β-hydroxyandrost-5-en-17-one (VII). M.p. 137°, $[a]_D=-71.9°$ (c=1.5) ([48]: m.p. 140°-141°, $[a]_D=-68°$. IR. ($CDCl_3$): 3600m, 3420m br., 1670w, 1590w, —$^1$H-NMR (360 MHz): 0.80 (s, 3 H); 1.05 (s, 3 H); 3.53 (m, $w_{½}\approx 22$, 1 H); 5.38 (m, 1 H); 5.72 (m, 1 H); 5.86 (m, 1 H).

Example 8—19-nor-Androsta-4,16-dien-3-one (9)

This synthesis is depicted in FIG. 3. 19-Nor-testosterone (XIX) is commercially available, e.g. from Chemical Dynamics Corp. It provides the starting material for 19-Nor-16-androsten derivatives. 19-Nor-testosterone (XIX) (Chemical Dynamics Corp.) was converted into the known acetate (Hartman, J. A. et al., *J. Am. Chem.*

Soc. (1956) 78:5662) with acetanhydride and pyridine (a). A solution of this acetate (4.8 g, 15.17 mmol) in toluene (10 ml) was pyrolyzed (b) at 540° (200 Torr, slow $N_2$-stream) in a glass tube packed with quartz pieces. Chromatography of the crude pyrolysate (3.1 g) on silica gel (150 g) with $CH_2Cl_2$ gave 1.1 g (28%) of the homogenous oily ketone 9; $[a]_D=+57.9°$ (c=1) ([27]: m.p. 71°-73°). —IR. ($CHCl_3$): 1660s, 1615m, 1585w, —$^1$H-NMR. (90 Mhz): 0.84 (s, 3 H); 5.82 (m, 2 H); 5.87 (br. s, 1 H).

Example 9—19-nor-$\Delta^{16}$Androsten-3-one (10)

This synthesis is depicted in FIG. 3. 19-Nortestosterone was reduced to 19-Nor-5α-androstan-17-ol-3-one (XX) with Lithium and ammonia (c) according to the method of Villotti, R., et al. (*J. Am. Chem. Soc.* (1960) 82:5693). Androsta-5α,17-diol-3-one (XX) was converted into the known acetate (Hartman, J. A. et al., *J. Am. Chem. Soc.* (1956) 78:5662) with acetanhydride and pyridine (a). A solution of 17β-acetoxy-5α-Estrane-3-one (8.0 g, 25.1 mmol) in octane/acetone 10:1 (22 ml) was pyrolyzed (b) at 550° (200 Torr, slow $N_2$-stream). Chromatography of the crude product (5.4 g) on silica gel (600 g) with $CH_2Cl_2$ and recrystallization of the homogenous fractions from PE gave 3.13 g (48.3%) of the pure ketone 10. M.p. 51°-54°, $[a]_D=+72.8°$ (c=1.0). —IR. ($CHCl_3$): 1705s, 1585w, —$^1$H-NMR. (90 MHz): 0.79 (s, 3 H); 5.71 (m, 1 H); 5.87 (m, 1 H).

Example 10—19-nor-$\Delta^{16}$-Androsten-3α-ol (11)

This synthesis is depicted in FIG. 3. L-Selectride (d, lithium tri(sec-butyl)hydridoborate, 4 ml of a 1M solution in THF, 4 mmol) was added dropwise at 0° to a solution of ketone 10 (800 mg, 3.10 mmol) in dry ether (5 ml). After stirring for 1 h at 0°, water was added (10 ml). The boranes were oxidized by adding 10% aq. NaOH-solution (5 ml), followed by 30% aq. $H_2O_2$-solution (3 ml) and stirring for 3 h at RT. After workup (ether), the crude product (790 mg, ca. 9:1 mixture of 11 and 12) was chromatographed on silica gel with $CH_2Cl_2$ to give 700 mg (87%) of pure alcohol 11. M.p. 119°-120°→123°-124° (from PE), $[a]_D=+40.6°$ (c=1.0). —IR. ($CHCl_3$): 3640m, 3500 br., 1585w. —$^1$H-NMR. (90 Mhz): 0.78 (s, 3 H); 4.09 (m, $w_{1/2}\approx 8$, 1 H); 5.71 (m, 1 H), 5.87 (m, 1 H).

Example 11—19-nor-$\Delta^{16}$-Androsten-3β-ol (12)

This synthesis is depicted in FIG. 3. A solution of the ketone 10 (800 mg, 3.10 mmol) in dry ether (5 ml) was added dropwise at RT. to a slurry of $LiAlH_4$ (38 mg, 1 mmol) in ether (3 ml) (e). After 1 h, the mixture was hydrolyzed with 10% aq. $H_2SO_4$. After workup (ether), the crude product (802 mg, 9:1-mixture of 12 and 11) was chromatographed on silica gel with $CH_2Cl_2$. A small fraction of 11 (70 mg) was eluted first, followed by the main fraction of 12 (705 mg, 87%). M.p. 113°-115°, $[a]_D=+36.3°$ (c=1.0). —IR. ($CHCl_3$): 3640m, 3500 br., 1585w. —$^1$H-NMR. (90 MHZ): 0.78 (s, 3 H); 3.60 (m, $w_{1/2}\approx 20$, 1 H); 5.71 (m, 1 H), 5.87 (m, 1 H).

Example 12—Syntheses of
19-OH-$\Delta^{4,16}$-Androstadien-3-one (18)

Figures 1, 5:
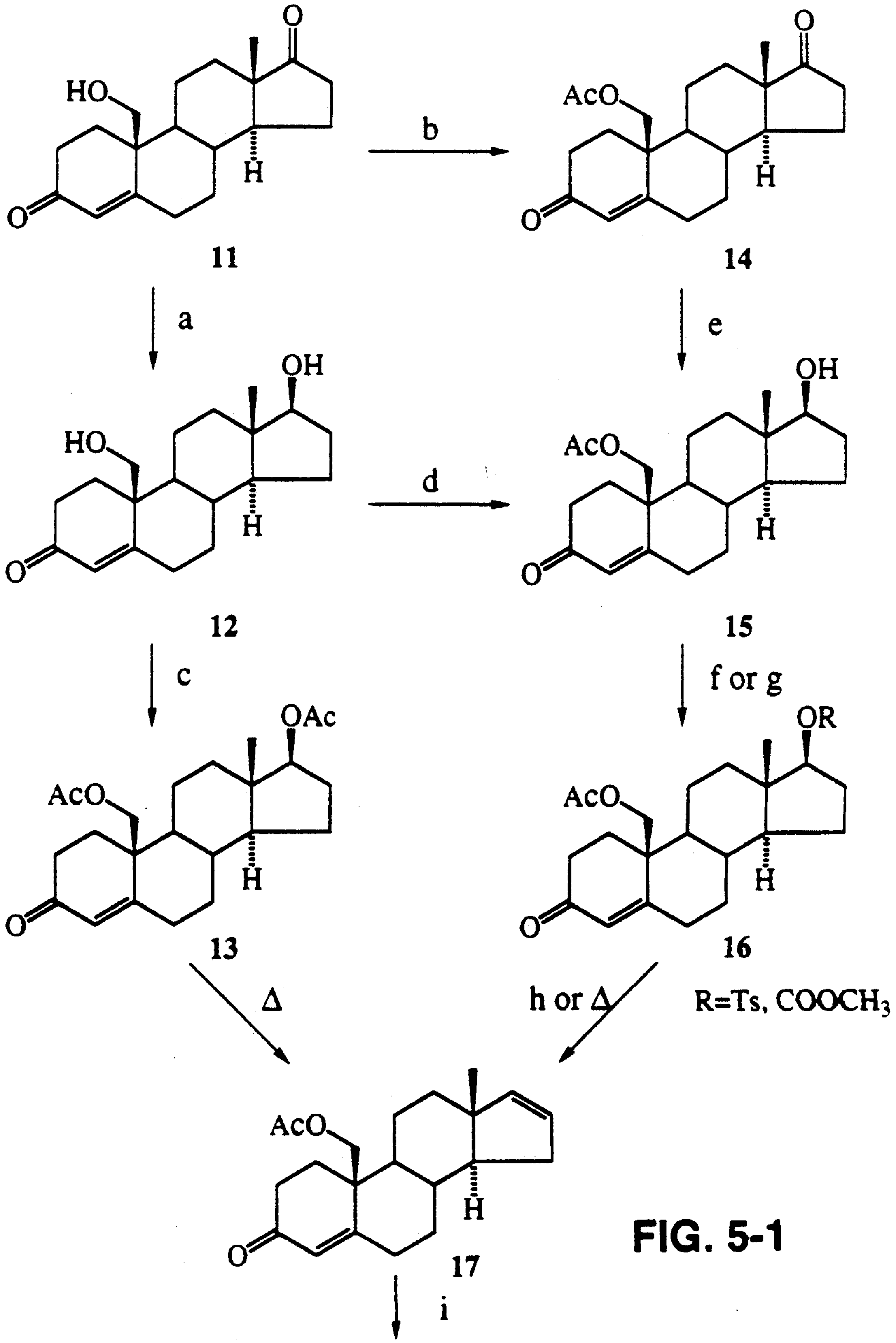
FIG. 5 schematically illustrates syntheses of 19-OH-Androsta-$\Delta^{4,16}$-dien-3-one.
Figures 2, 5:
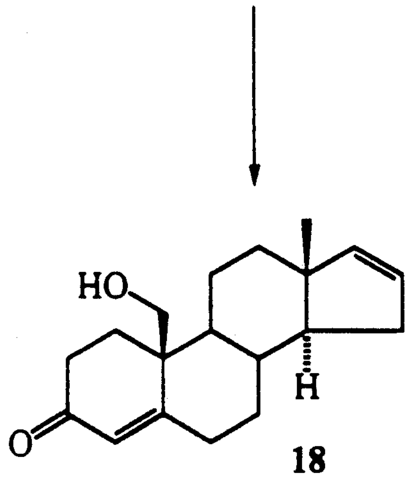

The following three methods of synthesis of 19-OH-$\Delta^{4,16}$-androstadien-3-one are depicted in FIG. 5.

Androst-4-en-17,19-diol-3-one (12):

Also known as 19-Hydroxytestosterone, this compound is commercially available from Steraloids, Inc. Alternatively, 19-hydroxyandrost-4-en-3,17-dione (11) is treated with potassium borohydride ($KBH_4$, a) in ethanol at −10° to 0° C. Aqueous work up is followed by extraction and purification to yield 19-hydroxytestosterone (12).

19-Acetoxyandrost-4-en-3,17-dione (14):

Androst-4-en-19-ol-3,17-dione (11) is treated with acetic anhydride ($Ac_2O$, b) in pyridine. Aqueous work-up is followed by extraction and purification to yield the acetate (14).

19-Acetoxytestosterone acetate (13):

19-Hydroxytestosterone (12) is treated with $Ac_2O$ in pyridine (c) with 4,4-dimethylaminopyridine catalyst. Aqueous work-up is followed by extraction and purification to yield the acetate (13).

19-Acetoxytestosterone (15) (method 1):

19-Hydroxytestosterone (12) is treated with $Ac_2O$ in pyridine (d). Aqueous work-up is followed by extraction and purification to yield the acetate (15).

19-Acetoxytestosterone (15) (method 2):

19-Acetoxyandrost-4-ene-3,17-dione (14) is treated with $KBH_4$ (e) in ethanol at −10° to 0° C. Aqueous work-up is followed by extraction and purification to yield the acetate (15).

19-Acetoxytestosterone tosylate (16,R=Ts):

19-Acetoxytestosterone (15) is treated with p-Toluenesulfonyl chloride (TsCl, f) in pyridine. Aqueous work-up is followed by extraction and purification to yield the tosylate (16,R=Ts).

19-Acetoxytestosterone methyl carbonate (16,R=$COOCH_3$):

19-Acetoxytestosterone (15) is treated with methyl chloroformate ($ClCOOCH_3$, g) in pyridine. Aqueous work-up is followed by extraction and purification to yield the methyl carbonate (16,R=$COOCH_3$).

19-Acetoxyandrosta-4,16-dien-3-one (17) (method 1):

19-Acetoxytestosterone acetate (13) is subjected to pyrolysis. The crude pyrolysate is purified to give the acetate (17).

19-Acetoxyandrosta-4,16-dien-3-one (17) (method 2):

19-Acetoxyandrone tosylate (16,R=Ts) is heated in 2,4,6-collidine (h). After cooling, aqueous work-up is followed by extraction and purification to yield the acetate (17).

19-Acetoxyandrosta-4,16-dien-3-one (17) (method 3):

19-Acetoxytestosterone methyl carbonate (16,R=$COOCH_3$) is subjected to pyrolysis. The crude pyrolysate is purified to give the acetate (17).

19-Hydroxyandrosta-4,16-dien-3-one (18):

19-Acetoxyandrosta-4,16-dien-3-one (17) is treated with potassium hydroxide in methanol (i). Aqueous work-up is followed by extraction and purification to yield the alcohol (18).

Example 13—Alternate synthesis of
19-OH-$\Delta^{4,16}$-Androstadien-3-one (22)

Figure 6:
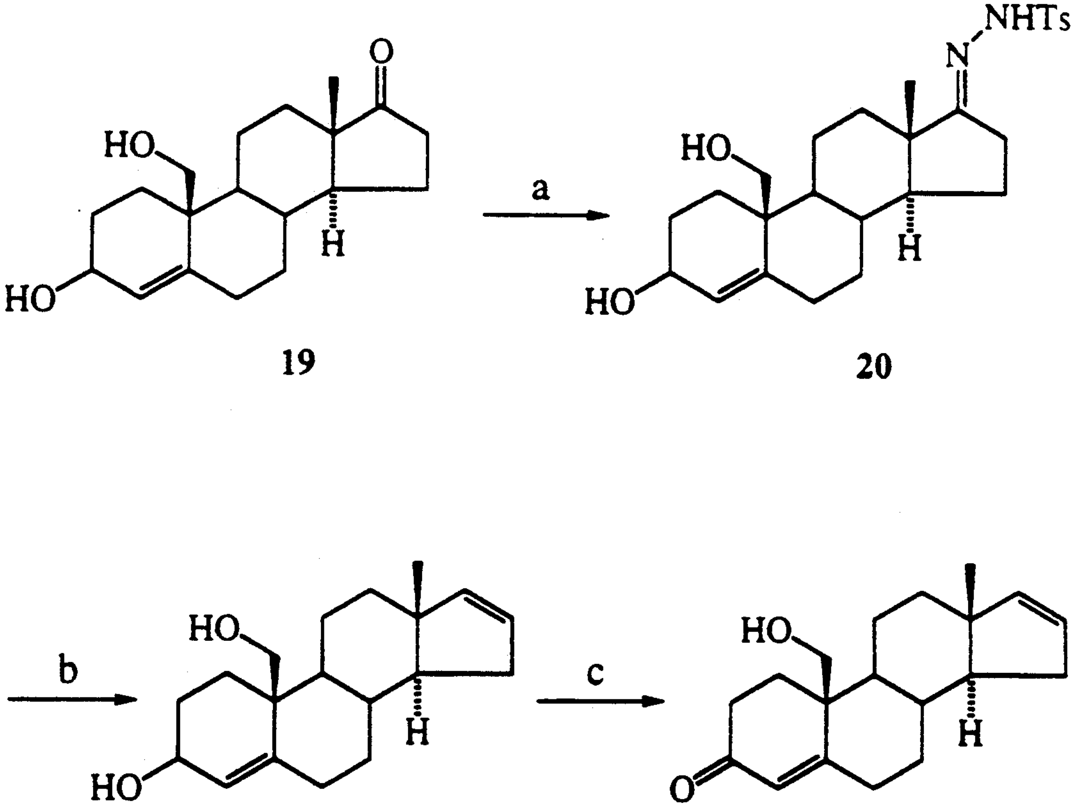
FIG. 6 schematically illustrates an alternate synthesis of 19-OH-Androsta-$\Delta^{4,16}$-dien-3-one.

The following method of synthesis is depicted in FIG. 6:

3,19-Dihydroxyandrost-4-en-17-one tosylhydrazone (20)

3,19-Dihydroxyandrost-4-en-17-one (19) is heated under reflux in methanol with one equivalent of p-toluenesulfonylhydrazide ($TsNHNH_2$, a) for 16 hours. After cooling, the mixture is evaporated to give the crude product. Purification yields the tosylhydrazone (20).

3,19-Dihydroxyandrosta-4,16-diene (21)

The tosylhydrazone (20) in tetrahydrofuran is treated with n-butyl lithium (BuLi, b) in hexane and the mixture is stirred at room temperature for 16 hours. Aqueous work up is followed by extraction and purification to yield the diene (21).

19-Hydroxyandrosta-4,16-dien-3-one (22)

3,19-Dihydroxyandrosta-4,16-diene (21) is treated with manganese dioxide ($MnO_2$, c) in hexane. The mixture is filtered and evaporated to give the crude product. Purification yields the enone (22).

Example 14—Alternate synthesis of Androsta-4,16-dien-3-one (25)

Figure 8:
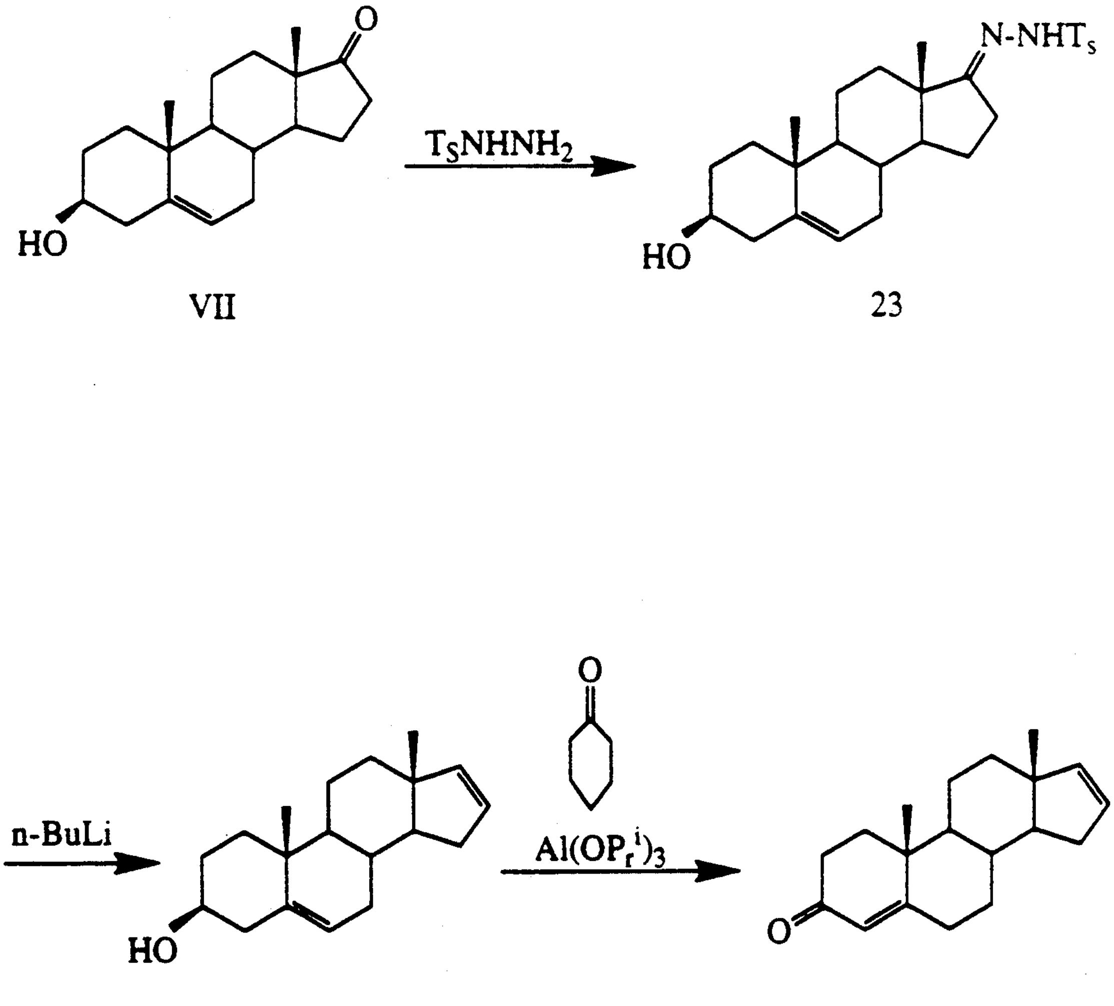
FIG. 8 schematically illustrates an alternate synthesis of Androsta-4,16-dien-3-one.

The following method of synthesis is depicted in FIG. 8:

Dehydroepiandrosterone p-Toluenesulfonylhydrazone (23)

Dehydroepiandrosterone (VII) (14.4 g, 50.0 m mole) and p-toluenesulfonylhydrazide (12.75 g, 68.5 m mole) in dry methanol (300 ml) were heated under reflux for 20 hours. The mixture was transferred to a conical flask and allowed to cool. The crystalline product was filtered off under suction and washed with methanol (50 ml). Further crops of product were obtained by sequentially evaporating the filtrate to 75 ml and 20 ml, and allowing to crystallize each time. Total yield was 21.6 g (95%).

Androsta-5,16-dien-3β-ol (24)

Dehydroepiandrosterone p-toluenesulfonylhydrazone (23) (22.8g, 50.0 m mole) in dry tetrahydrofuran (1.0 liters) was cooled in a dry ice/isopropanol bath. The mixture was stirred while n-butyl lithium (125 ml of 1.6M solution in hexane, 200 m mole) was added. The mixture was allowed to warm to room temperature and was stirred for 24 hours. Water (50 ml) was added with cooling in ice. The mixture was poured into saturated ammonium chloride solution/ice (500 ml) and extracted with ether (×2). The organic layers were washed with saturated sodium bicarbonate solution (500 ml) and saturated sodium chloride solution (500 ml), dried ($MgSO_4$) and evaporated in vacuo to give the crude product. This was purified by flash chromatography on 190 g silica gel 60, 230–400 mesh, eluting with ethyl acetate/hexane (20:80→50:50) to give crystalline material. The product was recrystallized from methanol (45 ml)/3% hydrogen peroxide (8 ml) washing with methanol (30 ml)/water (8 ml) to give pure product (6.75 g, 50%).

Androsta-4,16-dien-3-one (25)

A solution of 10 g of Androsta-5,16-dien-3β-ol (24) in 475 cc of toluene and 75 cc of cyclohexanone was distilled (ca. 50 cc of distillate was collected) to eliminate moisture, 5 f of $Al(OPr^i)_3$ in 50 cc of toluene was added and the solution was refluxed for 1 hour. Water then was added, volatile components were removed by steam distillation and the residue was extracted with chloroform. Evaporation of the dried extract, followed by crystallization of the residue from chloroform-hexane, yielded 7.53 g of Androsta-4,16-dien-3-one (25). Another 0.97 g (total, 8.5 g, 86%) was obtained by chromatography of the mother liquor on neutral alumina.

Example 15—Synthesis of Estra-1,3,5(10),16-tetraen-3-ol (28)

Figure 7:
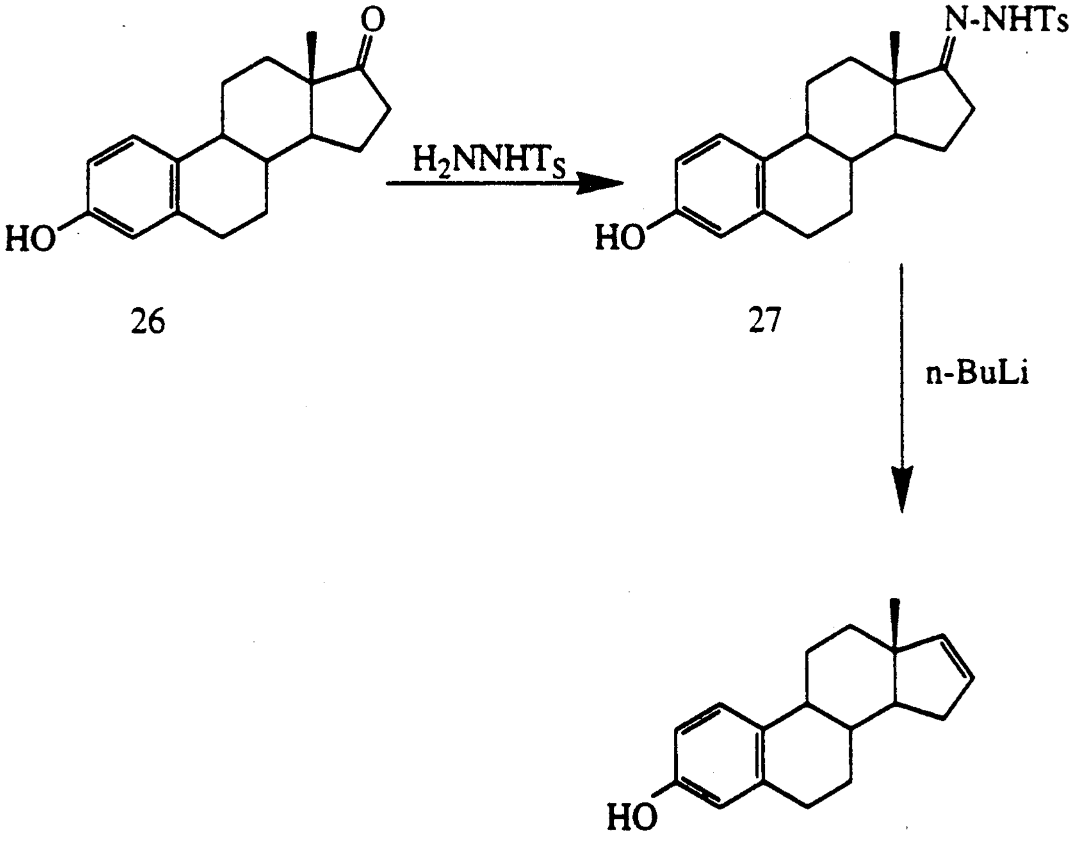
FIG. 7 schematically illustrates synthesis of 1,3,5(10),16-Estratetraen-3-ol.

The following method of synthesis is depicted in FIG. 7:

Estrone p-Toluenesulfonylhydrazone (27)

Estrone (26) (270 g, 1.00 mole) and p-toluenesulfonylhydrazide (232.8 g, 1.25 mole) in dry methanol (2.5 liters) were heated under reflux for 20 hours. The mixture was transferred to a conical flask and allowed to cool. The crystalline product was filtered off under suction and washed with methanol (300 ml). Further crops of product were obtained by sequentially evaporating the filtrate to 2000 ml, 800 ml and 400 ml, and allowing to crystallize each time. Total yield was 433.5 g (99%).

1,3,5(10),16-Estratetraen-3-ol (28):

Estrone p-toluenesulfonylhydrazone (27) (219.0 g, 500 m mole) in dry tetrahydrofuran (8.0 liters) was cooled in a sodium chloride/ice bath. The mixture was mechanically stirred while n-butyl lithium (800 ml of a 2.5M solution in hexane, 2.00 mole) was added via double-ended needle. The mixture was stirred at room temperature for 3 days. Ice (250 g) was added, followed by saturated ammonium chloride solution (500 ml). The phases were mixed by stirring and then allowed to settle. The aqueous phase was removed Via aspiration With teflon tube and extracted with ether (500 ml). The two organic phases were sequentially washed with the same batch of saturated sodium bicarbonate solution (500 ml) followed by saturated sodium chloride solution (500 ml). The organic layers were dried ($MgSO_4$) and evaporated in vacuo to give crude product. This was subjected to flash filtration on 500 g silica gel 60, 230–400 mesh, eluting with ethyl acetate/hexane (25:75, 2.5 liters). The filtrate was evaporated in vacuo to give crystalline material. The product was recrystallized from methanol (300 ml)/water (75 ml) washing with methanol (80 ml)/water (20 ml). Further recrystallization from ethyl acetate/hexane (12.5:87.5) gave pure product (88.9 g, 70%).

Example 16—Electrophysiology of 16-Androstene Stimulation of the Human VNO and Olfactory Epithelium A non-invasive method has been employed to record local electrical potentials from the human vomeronasal organ (VNO) and from the olfactory epithelium (OE). Localized gaseous stimulation was applied to both nasal structures at different instances using specially designed catheter/electrodes connected to a multichannel drug delivery system. The local response of the VNO and the OE showed a correlation with the concentration of the stimulus.

The study was performed on ten clinically normal (screened) volunteers—2 males and 8 females, ranging in age from 18 to 85 years. The studies were conducted without general or local anesthetics.

The catheter/electrodes were designed to deliver a localized stimulus and simultaneously record the response. In the case of VNO recording, the right nasal fosa of the subject was explored using a nasoscope (nasal specula) and the vomeronasal opening was localized close to the intersection of the anterior edge of the vomer and the nasal floor. The catheter/electrode was gently driven through the VNO-opening and the electrode tip placed in the organ's lumen at 1 to 3 mm from the opening. The nasoscope was then removed. In the case of the OE, recording the procedure was similar except the positioning of the catheter/electrode was gently placed deep in the lateral part of the medial nasal duct, reaching the olfactory mucosa.

Localized gaseous stimulation was done through the catheter/electrode. A constant stream of clean, non-odorous, humidified air at room temperature was continuously passed through a channel of the stimulating system. The stimulating substances were diluted in propylene glycol, mixed with the humidified air, and puffed for from 1 to 2 seconds through the catheter-/electrode. It is estimated that this administration provides about 25 picogram of steroid to the nasal cavity.

Figure 9A:
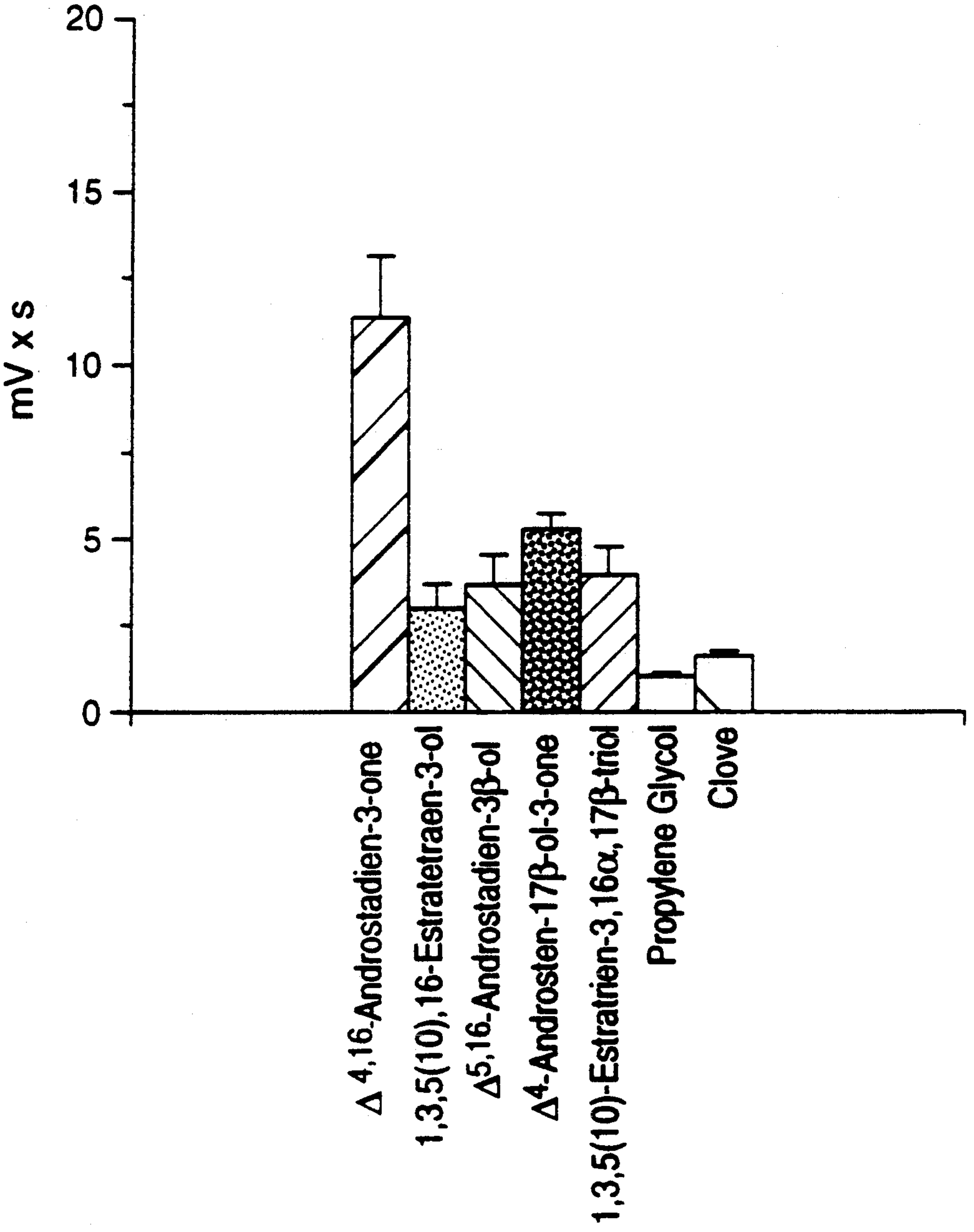
FIG. 9 is a graphic representation of the electrophysiological effect of the localized administration of particular 16-Androstene steroids to the vomeronasal organ and to the olfactory epithelium.
Figure 9B:
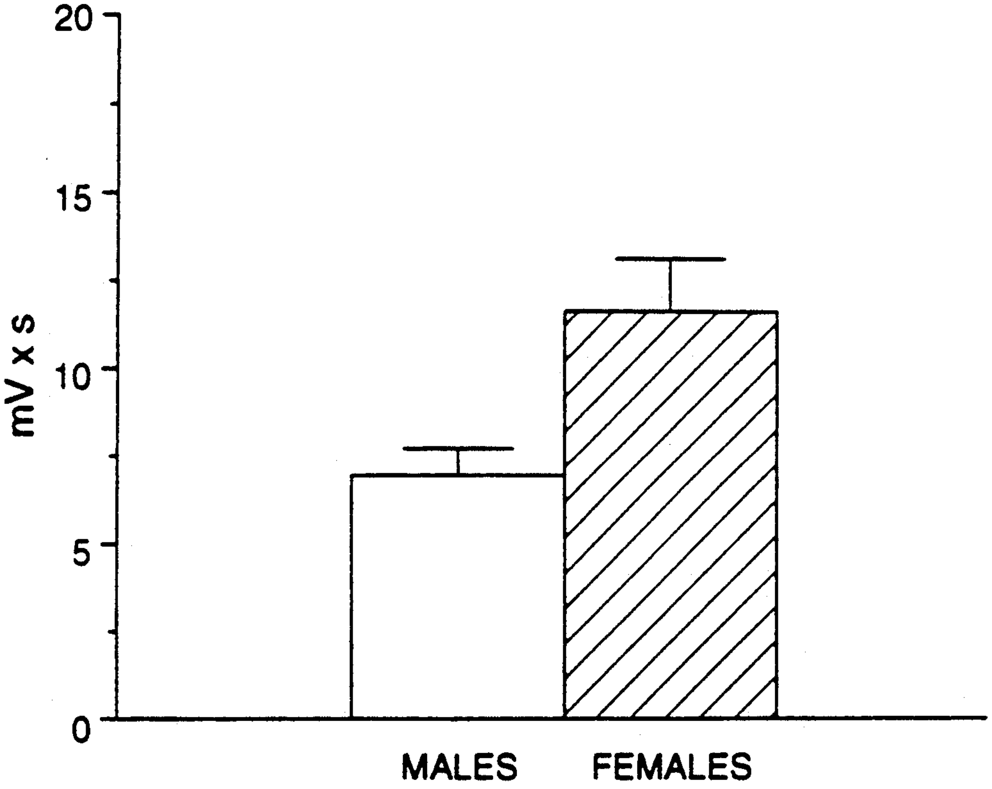
Figure 9C:
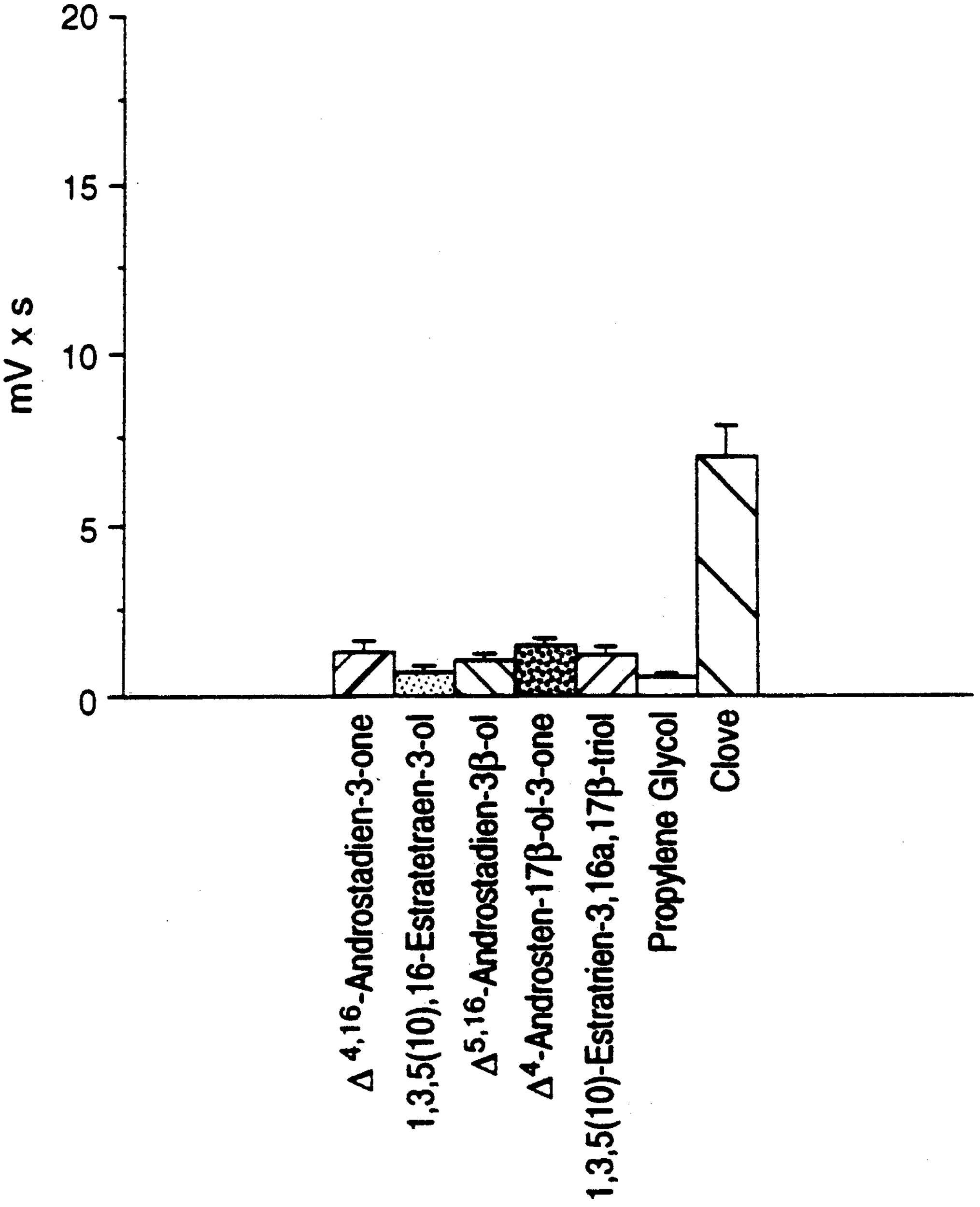
Figure 10A:
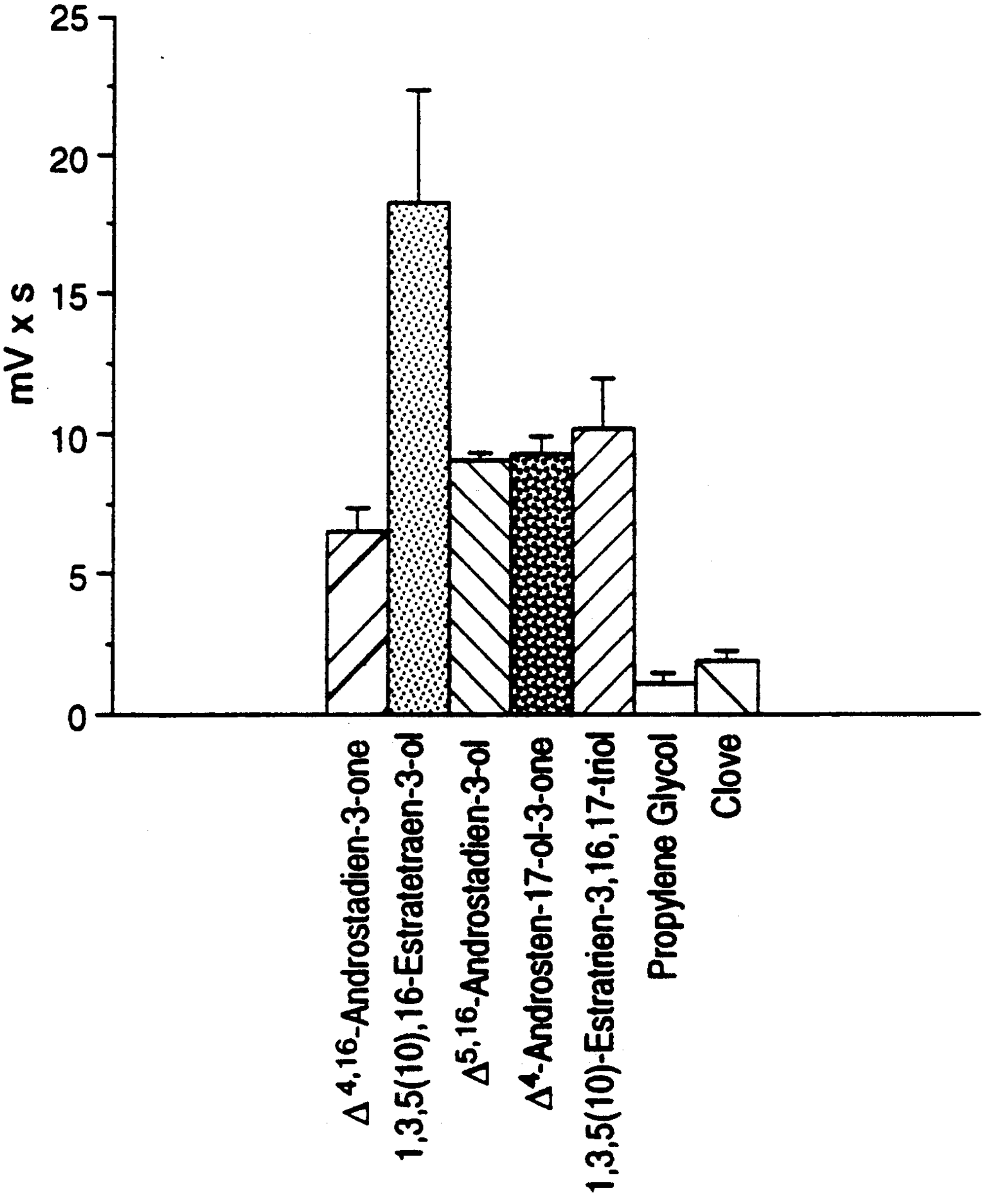
FIG. 10 is a graphic representation of the electrophysiological effect of the localized administration of particular Estrene steroids to the vomeronasal organ and to the olfactory epithelium.
Figure 10B:
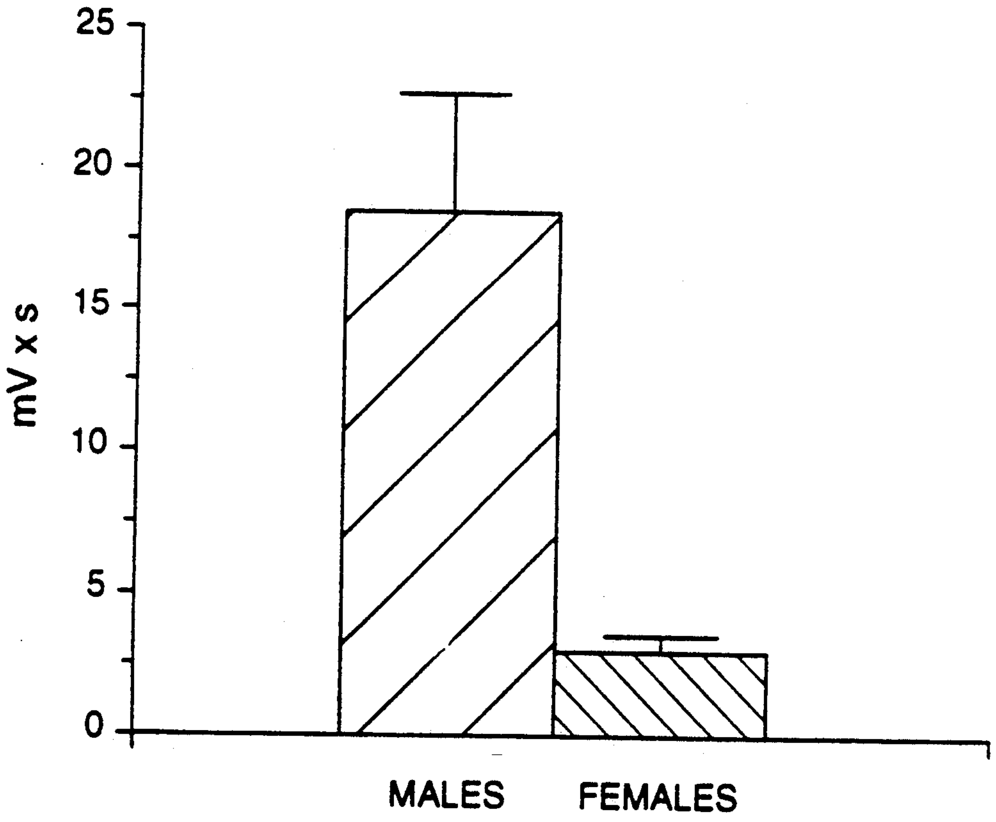
Figure 10C:
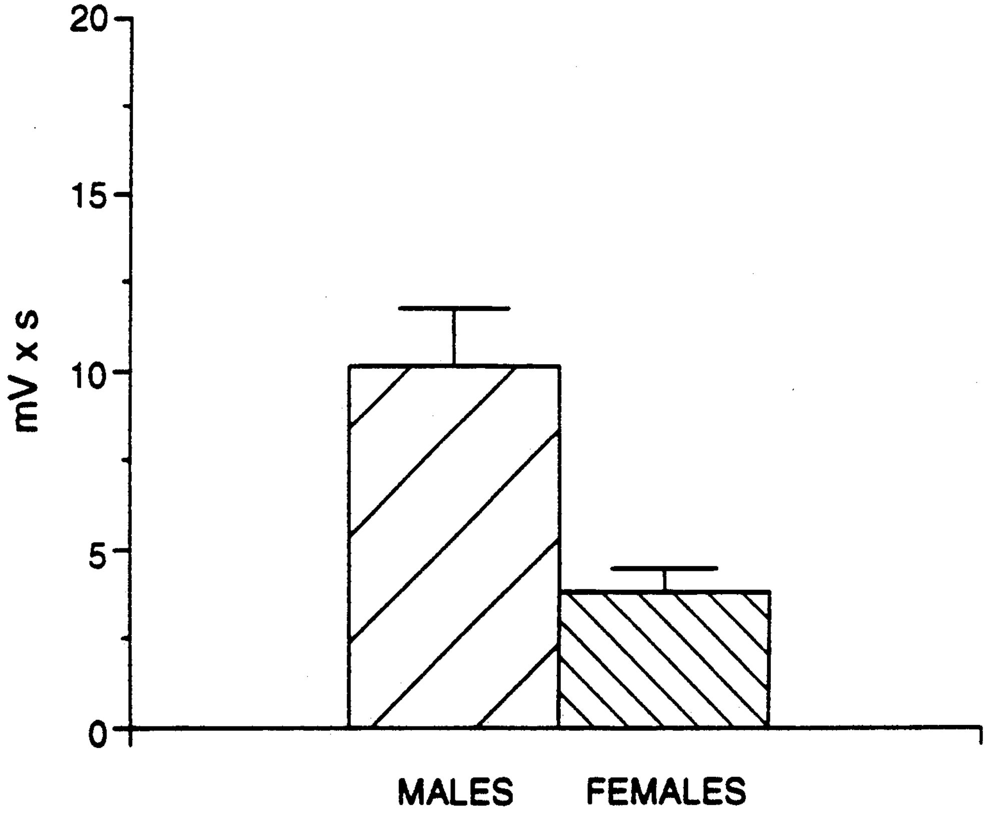
Figure 10D:
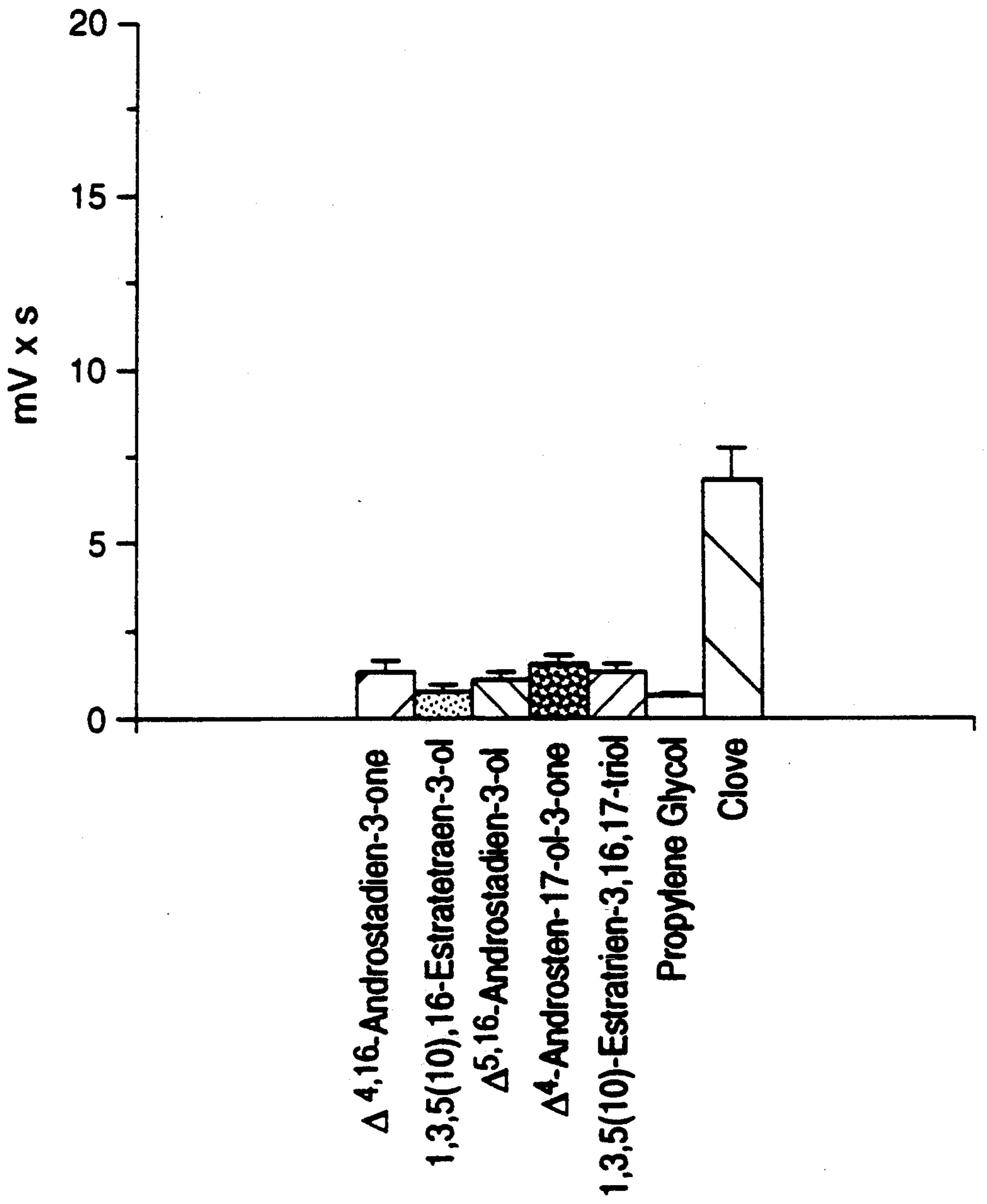

The results of this study are presented in FIG. 9. The response is a negative potential measured in millivolt-seconds (mV×S). Δ4,16-androstadien-3-one elicits a significantly stronger VNO response in females than do the other compounds tested (FIG. 9A). Furthermore, the VNO response to Δ4,16-androstadien-3-one is sexually dimorphic—twice as strong in females as it is in males (FIG. 9B). In contrast, the OE response in both males and females is low compared to a strong odorant such as clove (FIG. 9C).

Example 17—Electrophysiology of Estrene Stimulation of the Human VNO and Olfactory Epithelium A non-invasive method has been employed to record local electrical potentials from the human vomeronasal organ (VNO) and from the olfactory epithelium (OE). Localized gaseous stimulation was applied to both nasal structures at different instances using specially designed catheter/electrodes connected to a multichannel drug delivery system. The local response of the VNO and the OE showed a correlation with the concentration of the stimulus.

The study was performed on ten clinically normal (screened) volunteers—2 males and 8 females, ranging in age from 18 to 85 years. The studies were conducted without general or local anesthetics.

The catheter/electrodes were designed to deliver a localized stimulus and simultaneously record the response. In the case of VNO recording, the right nasal fosa of the subject was explored using a nasoscope (nasal specula) and the vomeronasal opening was localized close to the intersection of the anterior edge of the vomer and the nasal floor. The catheter/electrode was gently driven through the VNO-opening and the electrode tip placed in the organ's lumen at 1 to 3 mm from the opening. The nasoscope was then removed. In the case of the OE, recording the procedure was similar except the positioning of the catheter/electrode was gently placed deep in the lateral part of the medial nasal duct, reaching the olfactory mucosa.

Localized gaseous stimulation was done through the catheter/electrode. A constant stream of clean, non-odorous, humidified air at room temperature was continuously passed through a channel of the stimulating system. The stimulating substances were diluted in propylene glycol, mixed with the humidified air, and puffed for from 1 to 2 seconds through the catheter-/electrode. It is estimated that this administration provides about 25 picograms of steroid to the nasal cavity.

The results of this study are presented in FIG. 10. The response is a negative potential measured in millivolt-seconds (mV×S). 1,3,5(10),16-Estratetraen-3-ol elicits a significantly stronger VNO response in males than do the other compounds tested (FIG. 10A). 1,3,5(10)-Estratriene-3,16α,17β-triol also elicits a strong VNO response. Furthermore, the VNO response to these two estrenes is sexually dimorphic—approximately four times as strong in males as it is in females (FIG. 10B). In contrast, the OE response in both males and females is low compared to a strong odorant such as clove (FIG. 10C).

It will be apparent to those skilled in the art that the objects of this invention have been achieved by providing the compositions described herein. Various changes may be made in the structure of the pheromones and in the compositions containing pheromones without departing from the concept of the invention. Further, features of some compositions disclosed in this application may be employed with features of other compositions. Therefore, the scope of the invention is to be determined by the terminology of the following claims and the legal equivalents thereof.

I claim as my invention:

1. A non-therapeutic fragrance composition comprising an odorant and at least one human pheromone selected from a 16-Androstene steroid which has the formula:

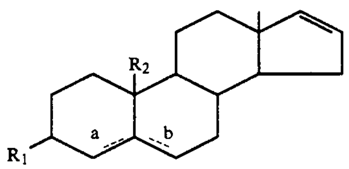

I wherein $R_1$ is selected from the group consisting of oxo, α-hydroxy, and β-hydroxy; and $R_2$ is selected from the group consisting of hydrogen, hydroxy, acyl, acyloxy, alkoxy, lower alkyl, methyl, hydroxyalkyl, hydroxymethyl, acyloxyalkyl, acyloxymethyl, alkoxyalkyl, and alkoxymethyl, and wherein "a" and "b" are alternative sites for an optional double bond, and at least one Estrene steroid which has the formula:

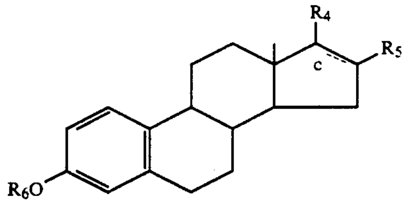

II wherein $R_4$ is selected from the group consisting of hydrogen, alkyl, oxo, α-hydroxy, β-hydroxy, sulfate, cypionate, acetate, and glucuronide, $R_5$ is selected from the group consisting of hydrogen, α-hydroxy, and β-hydroxy; $R_6$ is selected from the group consisting of hydrogen, lower alkyl, benzoyl, cypionyl, acetyl, glucuronide, lower acyl and sulfate; and "c" is an optional double bond; said pheromone generating an in vivo vomeronasal organ negative receptor binding potential in a human subject.

2. The fragrance composition of claim 1 wherein said negative receptor binding potential is no less than about 5 mV×S.

3. The fragrance composition of claim 1 wherein said negative receptor binding potential is no less than about 10 mV×S.

4. The fragrance composition of claim 1 wherein said pheromone is selected from the group consisting of 19-nor-16-Androsten-3-one, 19-nor-16-Androsten-3α-ol, and 19-nor-16-Androsten-3β-ol, and mixtures thereof.

5. The fragrance composition of claim 4 wherein the concentration of said pheromone in the fragrance composition is at least about 100 ng/ml, but no more than about 100 μg/ml.

6. The fragrance composition of claim 5 wherein the concentration of said pheromone in the fragrance is at least about 1 μg/ml, but no more than about 25 μg/ml.

7. The fragrance composition of claim 4 wherein said composition is formulated for external application to the skin.

8. The fragrance composition of claim 7 wherein the composition is a perfume.

9. A fragrance composition comprising at least one human pheromone selected from the group consisting of 16-Androstene steroids having the formula:

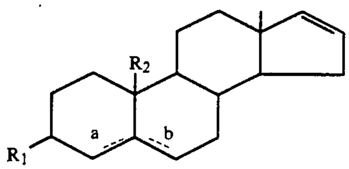

I wherein $R_1$ is selected from the group consisting of oxo, α-hydroxy, and β-hydroxy; and $R_2$ is selected from the group consisting of hydrogen, hydroxy, acyl, acyloxy, alkoxy, lower alkyl, methyl, hydroxyalkyl, hydroxymethyl, acyloxyalkyl, acyloxymethyl, alkoxyalkyl, and alkyoxymethyl and wherein "a" and "b" are alternative sites for a double head.

10. The fragrance composition of claim 9 wherein the concentration of said pheromone in the fragrance composition is at least about 100 ng/ml, but no more than about 100 μg/ml.

11. The fragrance composition of claim 10 wherein the concentration of said pheromone in the fragrance composition is at least about 1 μg/ml, but no more than about 25 μg/ml.

12. The fragrance composition of claim 9 wherein said composition is formulated for external application to the skin.

13. The fragrance composition of claim 12 wherein the composition is a perfume.

14. A fragrance composition comprising at least one human pheromone selected from the group consisting of Estrene steroids having the formula:

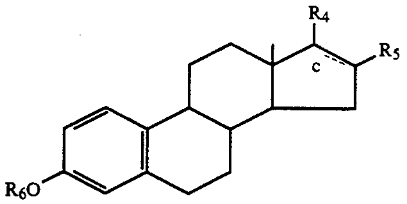

II wherein $R_4$ is selected from the group consisting of hydrogen, alkyl, oxo, α-hydroxy, β-hydroxy, sulfate, cypionate, acetate, and glucuronide; $R_5$ is selected from the group consisting of hydrogen, α-hydroxy, and β-hydroxy; $R_6$ is selected from the group consisting of hydrogen, lower alkyl, benzoyl, cypionyl, acetyl, glucuronide, lower acyl and sulfate; and "c" is an optional double bond.

15. The fragrance composition of claim 14 wherein the concentration of said pheromone in the fragrance composition is at least about 100 ng/ml, but no more than about 100 μg/ml.

16. The fragrance composition of claim 15 wherein the concentration of said pheromone in the fragrance composition is at least about 1 μg/ml, but no more than about 25 μg/ml.

17. The fragrance composition of claim 14 wherein said composition is formulated for external application to the skin.

18. The fragrance composition of claim 17 wherein the composition is a perfume.

19. The fragrance composition of claim 1 wherein said Androstene steroid is ${}^{4,16}$Androstadien-3-one and said Estrene steroid is 1,3,5(10),16-Estratetraen-3-ol.

20. The fragrance composition of claim 19 wherein the concentration of said pheromone in the fragrance composition is at least about 100 ng/ml, but no more than about 100 μg/ml.

21. The fragrance composition of claim 20 wherein the concentration of said pheromone in the fragrance composition is at least about 1 μg/ml, but no more than about 25 μg/ml.

22. The fragrance composition of claim 19 wherein said composition is formulated for external application to the skin.

23. The fragrance composition of claim 22 wherein the composition is a perfume.

* * * * *

UNITED STATES PATENT AND TRADEMARK OFFICE

CERTIFICATE OF CORRECTION

PATENT NO. : 5,278,141

DATED : January 11, 1994

INVENTOR(S) : David L. Berliner

It is certified that error appears in the above-identified patent and that said Letters Patent is hereby corrected as shown below:

Claim 9, column 19, line 37, delete "head" and replace with --bond--.

Signed and Sealed this

Twenty-eighth Day of April, 1998

Attest:

BRUCE LEHMAN

*Attesting Officer*

*Commissioner of Patents and Trademarks*